(12) United States Patent
Peuralahti et al.

(10) Patent No.: US 8,221,719 B2
(45) Date of Patent: Jul. 17, 2012

(54) LUMINESCENT LANTHANIDE (III) CHELATES, CHELATING AGENTS AND CONJUGATES DERIVED THEREOF

(75) Inventors: Jari Peuralahti, Turku (FI); Jari Hovinen, Raisio (FI); Janne Ketola, Turku (FI); Lassi Jaakkola, Littoinen (FI); Veli-Matti Mukkala, Kaarina (FI); Päivi Liitti, Turku (FI)

(73) Assignee: Wallac Oy, Turku (FI)

( * ) Notice: Subject to any disclaimer, the term of this patent is extended or adjusted under 35 U.S.C. 154(b) by 24 days.

(21) Appl. No.: 12/676,604

(22) PCT Filed: Sep. 5, 2008

(86) PCT No.: PCT/FI2008/050494
§ 371 (c)(1),
(2), (4) Date: Mar. 31, 2010

(87) PCT Pub. No.: WO2009/030819
PCT Pub. Date: Mar. 12, 2009

(65) Prior Publication Data
US 2010/0204442 A1 Aug. 12, 2010

(30) Foreign Application Priority Data
Sep. 5, 2007 (FI) .................................. 20070677

(51) Int. Cl.
*A61K 51/00* (2006.01)
*A61M 36/14* (2006.01)
(52) U.S. Cl. ...................... 424/1.65; 424/1.11; 424/1.49; 424/1.69; 424/1.73; 424/1.53; 534/7; 534/10; 534/11; 534/15
(58) Field of Classification Search .................. 424/1.11, 424/1.49, 1.53, 1.65, 1.69, 9.1, 9.2, 9.3, 9.4, 424/1.73; 534/7, 10–16; 206/223, 569, 570; 548/146, 215; 546/1; 549/1, 200; 540/450
See application file for complete search history.

(56) References Cited

FOREIGN PATENT DOCUMENTS

| WO | WO 2005/021538 | * | 3/2005 |
|---|---|---|---|
| WO | WO 2005/021538 A | | 3/2005 |
| WO | WO 2009/030819 A1 | | 3/2009 |

OTHER PUBLICATIONS

International Search Report, (2009).
Blomberg, K., Hautala, R., Lövgren J. et al.: "Time-resolved fluorometric assay for natural killer activity using target cells labelled with a fluoroscence ligand" in Journal of Immunological Methods 193 (1996) 199-206.
Dadabhoy, A., Faulkner, S., Sammes G.P: "Long wavelength sensitizers for europium(III) luminescence based on acridone derivatives" in J. Chem. Soc., Perkin Trans. 2, 2002, 348-357.
Duan, X-h., Liu, X-y, Guo, L-n. et al.: "Palladium-Catalyzed One-Pot Synthesis of Highly Substitued Furans by a Three-Component Annulation Reaction" in J. Org. Chem, 2005, 70, 6980-6983.
Fichna, J., Janecka, A.:"Synthesis of Target-Specific Radiolabeled Peptides for Diagnostic Imaging" in Bioconjugate Chem. 2003, 14, 3-17.
Hakala, H., Mukkala, V.-M., Sutela, T., Hovinen, J.: "Synthesis and properties of nanopheres copolymerised with luminescent europium(III) chelates" in Org. Biomol. Chem., 2006, 4,1383-1386.
Hemmilä, I., Mukkala, V.-M., Latva, M., Kiilholma, P.: "Di- and tetracarboxylate derivatives of pyridines, bipyridines and terpyridines as luminogenic reagents for time-resolved fluorometric determination of terbium adn dysprosium" in Journal of Biochemical and Biophysical Methods, 26 (1993) 283-290.
Latva, M., Takalo, H., Mukkala, V.-M. et al.: "Correlation between the lowest triplet state energy level of the ligand and lanthanide(III) luminescence quantum yield" in Journal of Luminescence 75 (1997) 149-169.
Mukkala, V.-M., Helenius, M., Hemmilä, I.: "Development of Luminescent Europium(III) and Terbium(III) Chelates of 2,2':6',2"-Terpyridine Derivatives for Protein Labelling" in Helvetica Chimica Acta—vol. 76, (1993), pp. 1361-1378.
Soukka, T., Härmä, H., Paukkunen, J., Lövgren, T.: "Utilization of Kinetically Enhanced Monovalent Binding Affinity by Immunoassays based on Multivalent Nanoparticle-Antibody Bioconjugates" in Anal. Chem. 2001, 73; 2254-2260.
Takalo, H. and Hemmilä, I.: "Synthesis and Luminescence of Novel EuIII Complexing Agents and Labels with 4-(Phenylethynyl)pyridine Subunits" in Helvetica Chimica Acta—vol. 79 (1993), pp. 789-802.

* cited by examiner

Primary Examiner — D L Jones
(74) Attorney, Agent, or Firm — Seppo Laine Oy; Joshua P. Wert

(57) ABSTRACT

This invention relates to a group of novel chelating agents, novel chelates, biomolecules labeled with said chelates or chelating agents as well as solid supports conjugated with said chelates, chelating agents or labeled biomolecules. Especially the invention relates to novel chelating agents useful in solid phase synthesis of oligonucleotides or oligopeptides and the oligonucleotides and oligopeptides so obtained.

13 Claims, 9 Drawing Sheets

US 8,221,719 B2

LUMINESCENT LANTHANIDE (III) CHELATES, CHELATING AGENTS AND CONJUGATES DERIVED THEREOF

FIELD OF THE INVENTION

This invention relates to a group of novel chelating agents, novel chelates, biomolecules labeled with said chelates or chelating agents as well as solid supports conjugated with said chelates, chelating agents or labeled biomolecules.

BACKGROUND OF THE INVENTION

The publications and other materials used herein to illuminate the background of the invention, and in particular, cases to provide additional details respecting the practice, are incorporated by reference.

The use of long life-time emitting lanthanide(III) chelate labels or probes together with time-resolved fluorometry in detection provides a method to generate sensitive bioaffinity assays. Indeed, time-resolved fluorescence based on lanthanide(III) chelates has become a successful detection technology, and it has been used in in vitro diagnostics for over two decades. Time-resolved fluorescence quenching assays based on energy transfer from a lanthanide(III) chelate to a nonfluorescent quencher have been applied in various assays of hydrolyzing enzymes as well as for nucleic acid detection. The different photochemical properties of europium, terbium, dysprosium and samarium chelates even enable the development of multiparametric homogenous assays.

Stable luminescent lanthanide(III) chelates consist of a ligand with a reactive group for covalent conjugation to bioactive molecules, an aromatic structure, which absorbs the excitation energy and transfers it to the lanthanide ion and additional chelating groups such as carboxylic or phosphonic acid moieties and amines. Unlike organic chromophores, these molecules do not suffer from Raman scattering or concentration quenching. This allows multilabeling and development of chelates bearing several light absorbing moieties.

A luminescent lanthanide(III) chelate has to fulfill several requirements a) the molecule has to be photochemically stable both in the ground and excited states, b) the molecule has to be kinetically stable, c) the molecule has to be chemically stable, d) the excitation wavelength has to be as high as possible, preferably over 330 nm, e) the molecule must have a high excitation coefficient in the excitation wavelength, f) the energy transfer from the ligand to the central ion has to be efficient, g) the luminescence decay time has to be long, h) the chelate should be readily soluble in water, i) the bioactive molecules have to retain their affinities after the coupling to the lanthanide chelate.

A number of attempts have been made to tune the photophysical properties of the chelate labels suitable for time-resolved fluorometric applications. These include e.g. stable chelates composed of derivatives of pyridines [U.S. Pat. No. 4,920,195, U.S. Pat. No. 4,801,722, U.S. Pat. No. 4,761,481, U.S. Pat. No. 4,459,186, EP 0770610], bipyridines [U.S. Pat. No. 5,216,134], terpyridines [U.S. Pat. No. 4,859,777, U.S. Pat. No. 5,202,423, U.S. Pat. No. 5,324,825] or various phenolic compounds [U.S. Pat. No. 4,670,572, U.S. Pat. No. 4,794,191] as the energy mediating groups and polycarboxylic acids as chelating parts. In addition, various dicarboxylate derivatives [U.S. Pat. No. 5,032,677, U.S. Pat. No. 5,055,578, U.S. Pat. No. 4,772,563], macrocyclic cryptates [U.S. Pat. No. 4,927,923, EP 493745A] and macrocyclic Schiff bases [EP 369000] have been disclosed.

It has been shown that an europium(III) chelate based on 1,4,7-triazacyclononane tethered to three phenylethynylpyridinyl chromophores has good luminescence properties: its luminescence yield ($\epsilon\Phi$) is significantly higher than that of the chelate constructed from a single chromophore [*Helv. Chim. Acta*, 1996, 79, 789]; also its kinetic and thermodynamic stabilities are high. However, the chelate disclosed is not suitable for biomolecule derivatization because it lacks the reactive group required for conjugation. Furthermore, the ethynyl groups are susceptible to photobleaching, which is a problem especially in applications based on fluorescence microscopy. The alkynyl groups may also react with additives needed in in vitro assays, especially the highly nucleophilic azide ion. Later, the above mentioned problems have been solved by substituting the phenylethynyl groups with furyl and trismethoxyphenyl subunits giving rise to luminescent chelates with europium and samarium as well as with terbium and dysprosium, respectively [U.S. patent application Ser. No. 11/004,061; U.S. patent application Ser. No. 10/928, 143].

The azamacrocycles disclosed still have some drawbacks: the aromatic chromophores decrease their solubility to water. Also, the excitation maxima of the furyl derivatives are only somewhat over 300 nm; a higher excitation wavelength would be desirable while developing simpler and less expensive detection instruments and reduce the significance of the background luminescence signal. Furthermore, shorter wavelengths are absorbed by biological materials such as nucleic acids and aromatic amino acids.

Azamacrocycles tethered to long wavelength sensitizers, such as aromatic heterocycles, have also been proposed [e.g. U.S. Pat. No. 6,344,360, WO2006/039505, WO2007/055700, *J. Chem. Soc. Perkin Trans* 2, 2002, 348]. However, the emission spectrum of chelates of this type is often divided into several peaks. This, in turn causes problems: a) the quantum yield is relatively low when narrow filters have to be used, such as in multilabel assays, b) the additional emission bands cause background signal in applications based on time-resolved fluorescence energy transfer, c) the intensive long wavelength emission lines limit the use of NIR acceptors.

Although organic chelators and their substituents have a significant effect on the photophysical properties of lanthanide(III) chelates, no general rules for the estimation of these effects are available. It has been proposed in U.S. Pat. No. 4,761,481 that electron releasing substituents in the aromatic moiety of phenyl and naphthyl substituted 2,6-[N,N-di(carboxyalkyl)aminoalkyl]pyridines have advantageous effects on the photophysical properties on their chelates with lanthanide ions. However, no experimental evidence was given. Later it has been shown that this is the case with various terbium(III) and dysprosium(III) chelates [U.S. patent application Ser. No. 11/004,061] but the corresponding europium (III) chelates are practically non-luminescent [Hemmilä et al., *J. Biochem. Biophys. Methods*, 1993, 26, 283]. Furthermore, in contrast to that proposed in U.S. Pat. No. 4,761,481 it has been shown that lanthanide chelates with electron releasing amino substituent in the aromatic moieties have low quantum yields [Takalo et al., *Helv. Chim. Acta*, 1993, 76, 877].

In several applications, covalent conjugation of the chelate to bioactive molecules is required. Most commonly, this is performed in solution by allowing an amino or mercapto group of a bioactive molecule to react with isothiocyanato, maleimido or N-hydroxysuccinimido derivatives of the label [Fichna, J., Janecka, A., *Bioconjugate Chem.*, 2003, 14, 3]. Since in almost all biomolecule labelings the reaction is performed with an excess of an activated label, laborious purification procedures cannot be avoided. Especially, when the attachment of several label molecules, or site-specific labeling in the presence of several functional groups of similar reactivity is required, the isolation and characterization of the desired biomolecule conjugate is extremely difficult, and often practically impossible.

The biomolecule conjugates used in many applications, such as homogenous quenching assays, have to be extremely pure, since even small amounts of fluorescent impurities considerably increase the luminescence background and reduce the detection sensitivity. Thus, it is highly desirable to perform the conjugation of biomolecules on solid phase, since most of the impurities can be removed by washings while the biomolecule is still anchored to the solid support, and once released into the solution, only one chromatographic purification is required.

Solution phase labeling of large biomolecules, such as proteins, cannot be avoided. In these cases, the labeling reaction has to be as selective, and the purification of the biomolecule conjugates as effective as possible.

OBJECTS AND SUMMARY OF THE INVENTION

In this invention, it was observed that the photophysical properties of lanthanide chelates with furylpyridyl subunits can be tailored with electron donating substituents in the furyl ring. The aqueous solubility of the chelates, in turn, can be enhanced by carboxylic or sulfonic acid functions in the said furyl ring. The same substitution effects can also be achieved with the corresponding thienyl derivatives.

Accordingly, one aspect of the present invention is to provide chelating agents and lanthanide chelates thereof, useful for labeling biomolecules for use as probes in time-resolved fluorescence spectroscopy, wherein the chromophore comprises at least one furyl or thienyl substituted pyridyl group, where the furyl or thienyl group is substituted with one or more, same or different, electron donating groups and optionally with a carboxylic or sulfonic acid group or an ester, an amide or a salt of said acids.

One aspect of this invention is to provide chelates which give fluorescence with different chelated lanthanide ions.

One aspect is to provide chelates or chelating agents suitable for labeling of biomolecules in solution.

Another object is to provide chelates and chelating agents suitable for labeling oligopeptides, oligonucleotides and other molecules simultaneously with their synthesis on a solid phase.

Another object is to provide biomolecules and solid supports labeled with the chelates and chelating agents according to this invention.

Thus, according to one aspect, the invention concerns a chelate comprising
   a lanthanide ion, $Ln^{3+}$
   a chromophoric moiety comprising one or more aromatic units, wherein at least one of the aromatic units is a furyl or thienyl substituted pyridyl group, wherein the furyl or thienyl group is substituted with one or more, same or different, electron donating groups and optionally with a carboxylic or sulfonic acid group or an ester, an amide or a salt of said acids, G, and wherein the chromophoric moieties are tethered directly to each other to form a terpyridyl group or are tethered to each other via a cyclic or acyclic N-containing hydrocarbon chain,
   a chelating part comprising at least two carboxylic acid or phosphonic acid groups, or esters, amides or salts of said acids, attached to an aromatic unit of the chromophoric moiety, either directly or via a cyclic or acyclic N-containing hydrocarbon chain, and
   a reactive group A, tethered to the chromophoric moiety or to the chelating part either directly or via a linker L, said reactive group A enabling binding to a biomolecule or to a functional group on a solid phase.

According to another aspect this invention concerns a chelating agent comprising
   a chromophoric moiety comprising one or more aromatic units, wherein at least one of the aromatic units is a furyl or thienyl substituted pyridyl, wherein the furyl or thienyl group is substituted with one or more, same or different, electron donating groups and optionally with a carboxylic or sulfonic acid ester or an amide of said acids, G', wherein the chromophoric moieties are tethered directly to each other to form a terpyridyl group or tethered to each other via a cyclic or acyclic N-containing hydrocarbon chain,
   a chelating part comprising at least two carboxylic acid or phosphonic acid groups, or esters or amides of said acids, attached to an aromatic unit of the chromophoric moiety, either directly or via a cyclic or acyclic N-containing hydrocarbon chain, and
   a reactive group A, tethered to the chromophoric moiety or to the chelating part either directly or via a linker L, said reactive group A enabling binding to a biomolecule or to a functional group on a solid phase.

According to another aspect, the invention concerns a biomolecule conjugated with a chelate or a chelating agent according to this invention.

According to another aspect, the invention concerns a solid support conjugated with a chelate, a chelating agent or a biomolecule labeled according to this invention.

According to another aspect, this invention concerns a labeled oligopeptide, or an organic molecule obtained by synthesis on a solid phase, by introduction of an appropriate chelating agent according to this invention into the oligopeptide structure on an oligopeptide synthesizer, followed by deprotection and optionally also the introduction of a metal ion.

According to another aspect, this invention concerns a labeled oligonucleotide, obtained by synthesis on a solid phase, by introduction of an appropriate chelating agent according to this invention into the oligonucleotide structure on an oligonucleotide synthesizer, followed by deprotection and optionally also the introduction of a metal ion.

DETAILED DESCRIPTION OF THE INVENTION

Definitions

As defined herein, "electron donating group" refers to an alkyl and an alkoxy group. The alkyl group can be linear or branched, like methyl, ethyl, n-propyl, i-propyl, n-butyl, t-butyl and sec-butyl. The alkoxy group can be linear or branched, like methoxy, ethoxy, n-propoxy, i-propoxy, n-butoxy, t-butoxy and sec-butoxy. The electron donating group can be tethered also to electron withdrawing groups like hydroxyl, carboxylic and sulfonic acid groups if the electron withdrawing group is separated from the furane or thiophene ring by one or more methylene groups.

Chelates

The preferred chelates of the present invention comprise a lanthanide ion, $Ln^{3+}$, a chromophoric moiety, a chelating part comprising at least two carboxylic acid or phosphonic acid groups, or esters, amides or salts of said acids, attached to an aromatic unit of the chromophoric moiety, either directly or via a cyclic or acyclic N-containing hydrocarbon chain, and a reactive group A, tethered to the chromophoric moiety or to the chelating part either directly or via a linker L, said reactive group A enabling binding to a biomolecule or to a functional group on a solid phase or is not present.

The lanthanide ion $Ln^{3+}$ is preferably europium, samarium, terbium or dysprosium. More preferably, the lanthanide ion $Ln^{3+}$ is europium, or samarium.

Chelating agents and metal chelates based thereon where the chromophoric moiety is a bivalent aromatic structure comprising one or more furyl or thienyl substituted pyridyl groups, wherein the furyl or thienyl group has additional substituents are new. The furyl or thienyl substituted pyridyl group is capable of absorbing light or energy and transferring the excitation energy to the chelated lanthanide ion, giving rise to a strong fluorescence. In addition to the furyl or thienyl substituted pyridyl group or groups, the chromophoric unit may comprise unsubstituted pyridyl groups, pyridyl groups bearing other substituents and/or other aromatic groups.

The furyl or thienyl group can be attached to the pyridine ring via its C2 atom, or via its C3 atom by using e.g. 3-(dihydroxyboryl)furan or 3-(dihydroxyboryl)thiophene derivatives instead of 2-(dihydroxyboryl)furan or 2-(dihydroxyboryl)thiophene derivatives, respectively, as the reagent in the synthesis strategy. In the compounds demonstrated by specific examples herein, the 4-position of the pyridyl group bears the furyl or thienyl substituent. Other positions of the pyridine ring may also be useful for substitution.

According to an embodiment of the invention, the chromophoric moiety comprises one or more aromatic units, wherein at least one of the aromatic units is a furyl or thienyl substituted pyridyl group, wherein the furyl or thienyl group is substituted with one or more, same or different, electron donating groups, and optionally with a carboxylic or sulfonic acid group or an ester, an amide or a salt of said acids, G, and wherein the chromophoric moieties are tethered directly to each other to form a terpyridyl group or are tethered to each other via a cyclic or acyclic N-containing hydrocarbon chain.

According to another embodiment, the chromophoric moiety comprises one, two or three pyridyl groups, wherein at least one of them is furyl or thienyl substituted, where the furyl or thienyl group is substituted with one or more, same or different, electron donating groups. In particular embodiment, the electron donating groups are linear or branched alkyl groups, such as methyl, ethyl, n-propyl, i-propyl, n-butyl, t-butyl and sec-butyl.

The pyridyl groups can be tethered directly to each other to form a terpyridyl group. Alternatively, the pyridyl groups are tethered to each other via N-containing hydrocarbon chains. The said N-containing hydrocarbon chain can be either cyclic or acyclic. In a particular embodiment the N-containing hydrocarbon chain is cyclic. Compounds according to this invention comprising three chromophoric moieties wherein the chromophoric moieties are linked to each other via a cyclic N-containing hydrocarbon chain e.g. compounds based on azacrowns, are suitable in assays based on energy transfer or quenching, because in their emission spectra the peak near 615 nm is dominant.

According to one embodiment the chromophoric moiety comprises one, two or three carboxylic or sulfonic acid groups or esters, amides or salts of said acids, G. The carboxylic or sulfonic acid group enhances the aqueous solubility of said chelate. It can also be used for covalent or noncovalent coupling of said chelate to bioactive molecules and solid supports.

The chelating agent or chelate must bear a reactive group A in order to enable covalent binding of the chelating agent or chelate to a biomolecule or to a solid support. However, there exist applications where no such covalent binding is necessary. Chelating compounds of this invention can also be used in applications where no reactive groups in the chelate are needed. One example of this kind of technology is demonstrated e.g. in Blomberg, et al., *J. Immunological Methods*, 1996, 193, 199. Another example where no reactive group A is needed is the separation of eosinophilic and basophilic cells [WO2006/072668]. In this application positively and negatively charged chelates bind with negatively and positively charged cell surfaces, respectively.

Yet another example where no linker is needed is the preparation of highly luminescent beads simply by swelling chelates into the polymer [e.g. Soukka et al., *Anal. Chem.*, 2001, 73, 2254].

Although in many applications a reactive group A could, in principle, be attached directly to the chromophoric group or to the chelating part, it is desirable, for steric reasons, to have a linker L between the reactive group A and the chromophoric group or chelating part, respectively. The linker L can also be attached to the carboxylic or sulfonic acid group G via an amide bond. The linker is especially important in case the chelate should be used in solid phase syntheses of oligopeptides and oligonucleotides, but it is desirable also when labeling biomolecules in solution.

According to one embodiment the linker L is formed from one to ten moieties, each moiety being selected from the group consisting of phenylene, alkylene containing 1-12 carbon atoms, ethynydiyl (—C≡C—), ethylenediyl (—C=C—), ether (—O—), thioether (—S—), amide (—CO—NH—, —CO—NR'—, —NH—CO— and —NR'—CO—), carbonyl (—CO—), ester (—COO— and —OOC—), disulfide (—SS—), sulfonamide (—SO$_2$—NH—, —SO$_2$—NR'—), sulfone (—SO$_2$—), phosphate (—O—PO$_2$—O—), diaza (—N=N—), and tertiary amine, wherein R' represents an alkyl group containing less than 5 carbon atoms.

According to one embodiment, the reactive group A is selected from the group consisting of isothiocyanate, bromoacetamido, iodoacetamido, maleimido, 4,6-dichloro-1,3,5-triazinyl-2-amino, pyridyldithio, thioester, aminooxy, azide, hydrazide, amino, alkyne, a polymerizing group, and a carboxylic acid or acid halide or an active ester thereof.

According to another embodiment, the reactive group A is selected from the group consisting isothiocyanate, bromoacetamido, iodoacetamido, maleimido, 4,6-dichloro-1,3,5-triazin-2-ylamino, pyridyldithio, thioester, aminooxy, azide, hydrazide, amino, alkyne, a polymerizable group, and a carboxylic acid or acid halide or an active ester thereof or

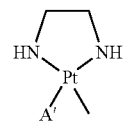

wherein A' is cleaving ligand like Cl, $(CH_3)_2SO$, $H_2O$, and $NO_3$ wherein - is the position of linker L.

In case the chelate or chelating agent should be attached to a microparticle or nanoparticle during the manufacturing process of said particles, the reactive group A is a polymerizable group, such as methacroyl group.

The lanthanide chelates to be polymerized to particles have to be soluble in organic solvents. This feature can be enhanced by omitting the carboxylic or sulfonic acid group G from the structures of the chelates according to this invention.

Furthermore, this allows the introduction of the third electron donating group to the furyl or thiophene subunits of said chelates.

In the case the chelate or chelating agent is to be attached to solid supports including nanomaterials, biomolecules, and various organic molecules using copper(I) catalyzed Huisgen-Sharpless dipolar [2+3] cycloaddition reaction, the reactive group A has to be either azide or terminal alkyne.

It has been proposed [U.S. Pat. No. 5,985,566] that oligonucleotides, DNA, RNA, oligopeptides, proteins and lipids can be transformed statistically by using label molecules tethered to platinum derivatives: In nucleic acids these molecules react predominantly at N7 of guanine residues. In this case the reactive group A is

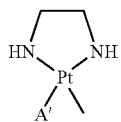

wherein A' is cleaving ligand like Cl, $(CH_3)_2SO$, $H_2O$, and $NO_3$

The group A-L- can be tethered to the molecule in different ways. It can be tethered to the chelating part, to the N-containing chain joining the aromatic units together, or to an aromatic unit. In the last mentioned case the group A-L- is tethered to a furyl or thienyl substituent either directly of via the carboxylic or sulfonic acid derivative G.

According to one embodiment, the chelated metal ion $Ln^{3+}$ is europium(III), samarium(III), terbium(III) or dysprosium (III). In an particular embodiment the chelated metal ion $Ln^{3+}$ is europium(III) and samarium(III)

Exemplary specific chelates according to this invention are the following structures:

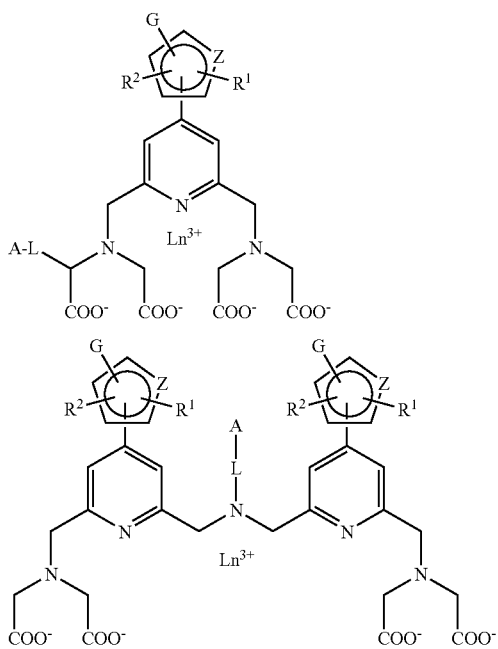

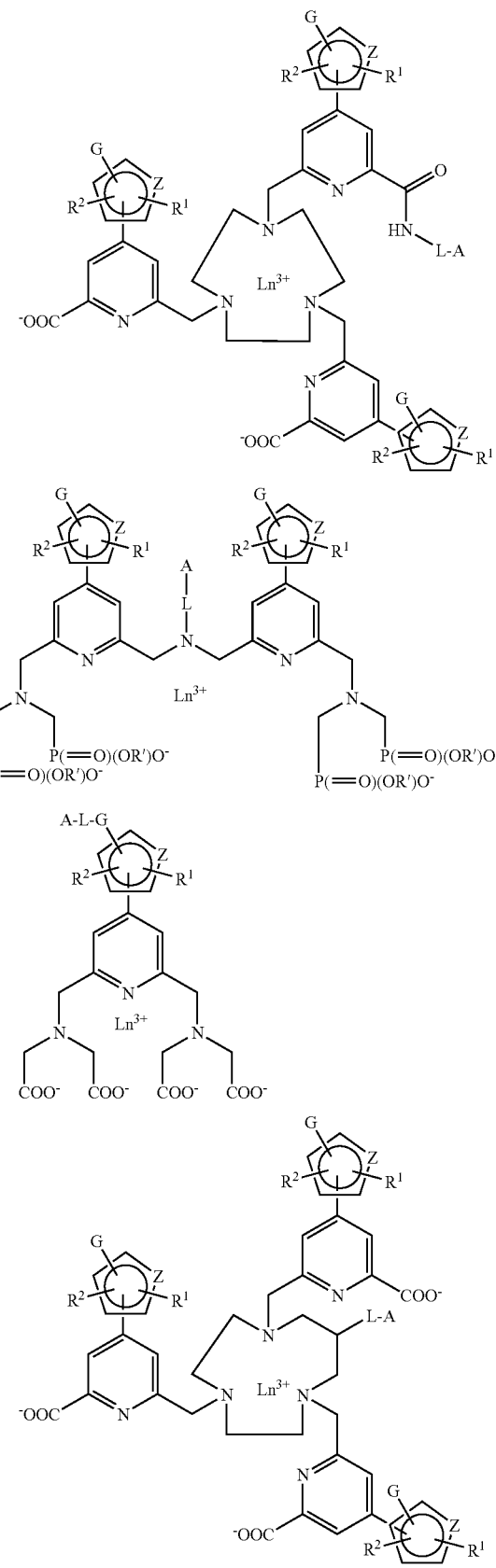

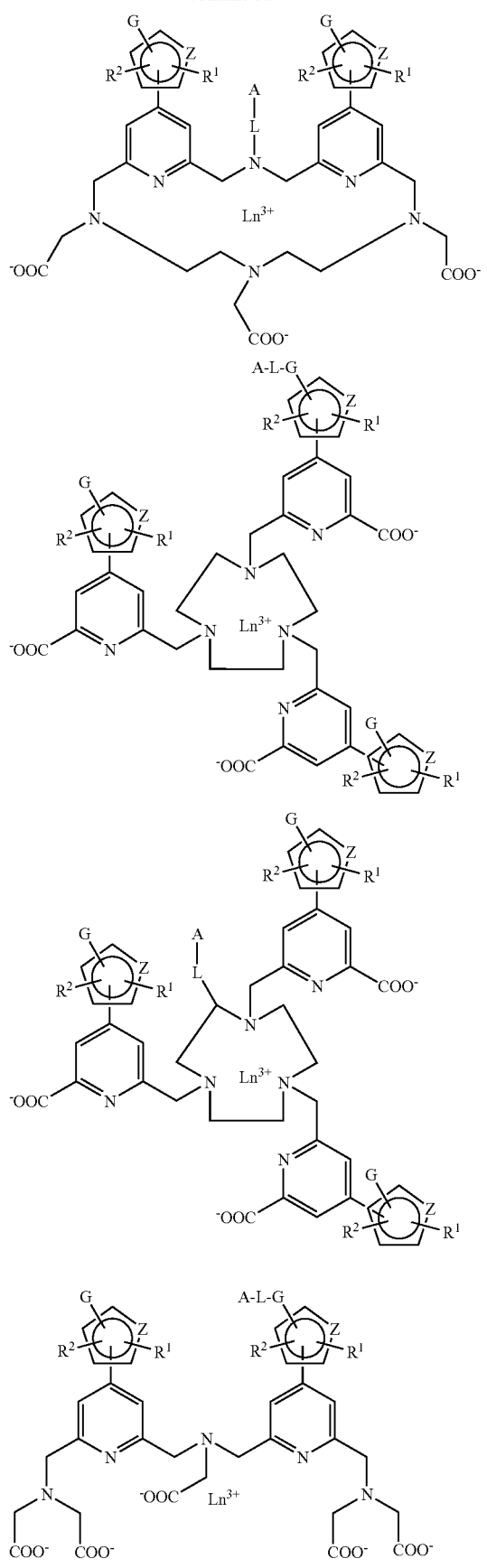
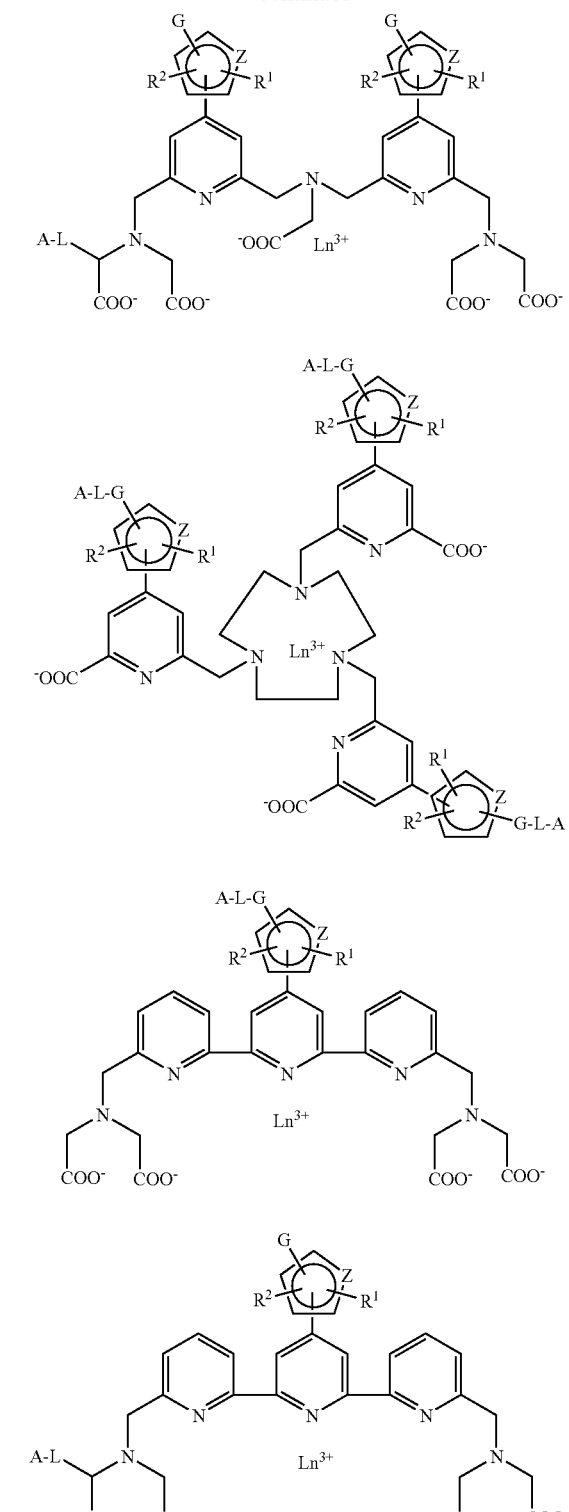
wherein $R^1$ and $R^2$ are same or different electron donating groups L, G, R' and A are defined as above, and Z in either O and S, for furyl and thienyl, respectively.
In a particular embodiment the chelate is selected from the following structures

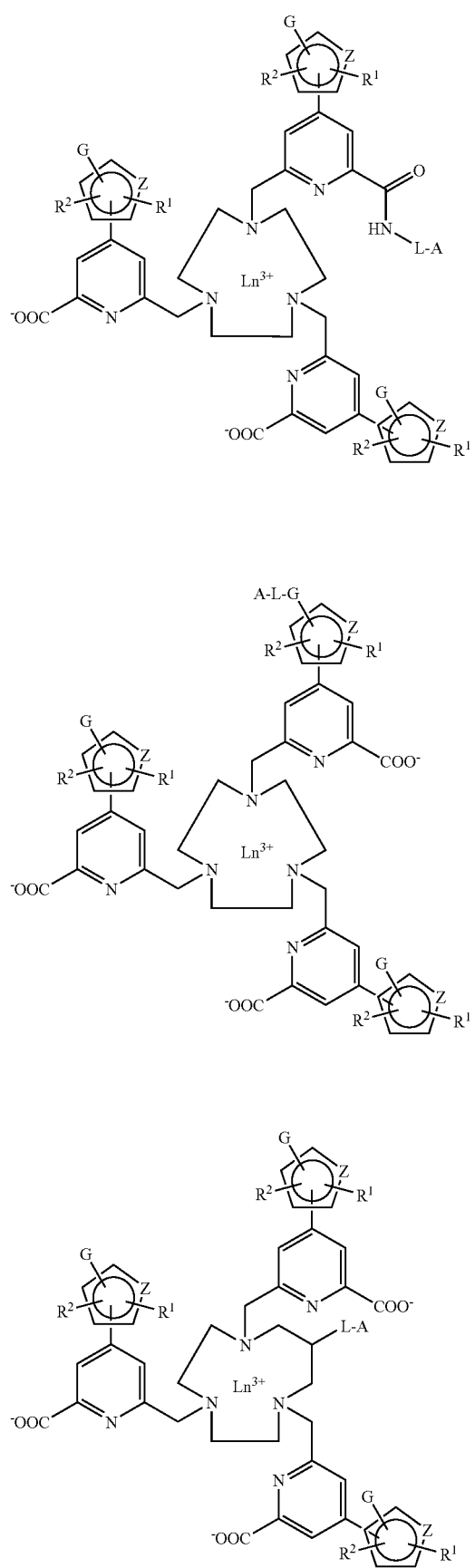
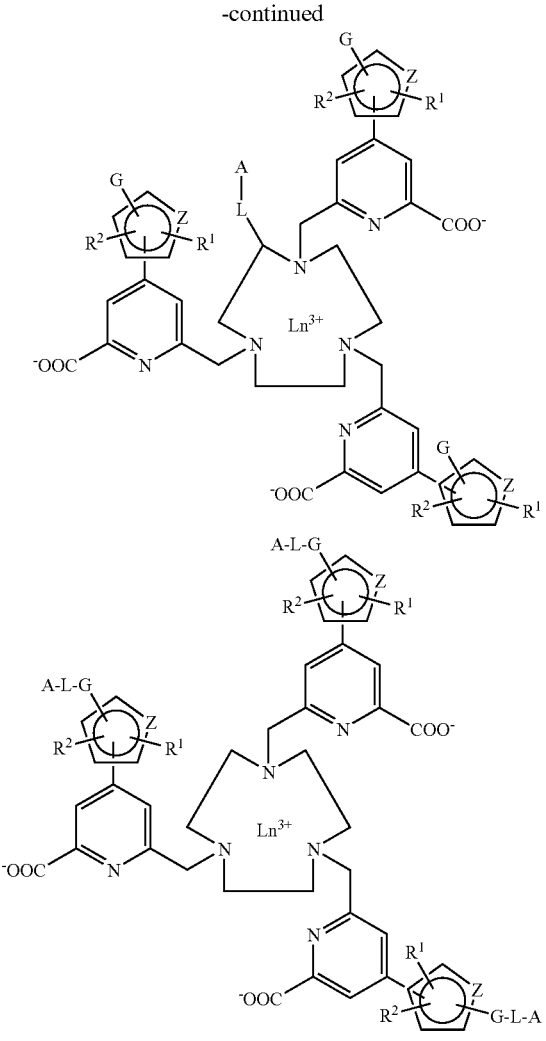

wherein $R^1$ and $R^2$ are same or different electron donating groups, L, G and A are defined as above, and Z in either O and S, for furyl and thienyl, respectively.

Chelating Agents for Use in Peptide Synthesis

According to one embodiment, the chelating agent according to this invention is suitable for use in the synthesis of an oligopeptide. In this application, the reactive group A is connected to the chelating agent via a linker L, and A is a carboxylic acid or its salt, acid halide or an ester or an amino acid residue —$CH(NHR^3)R^4$ where $R^3$ is a transient protecting group and $R^4$ is a carboxylic acid or its salt, acid halide or an ester. Exemplary chelating agents are the following structures

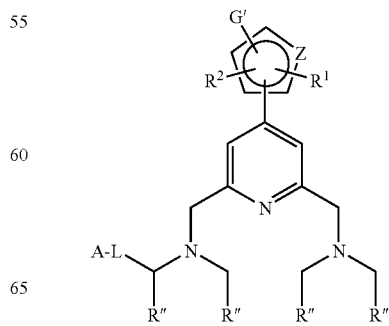

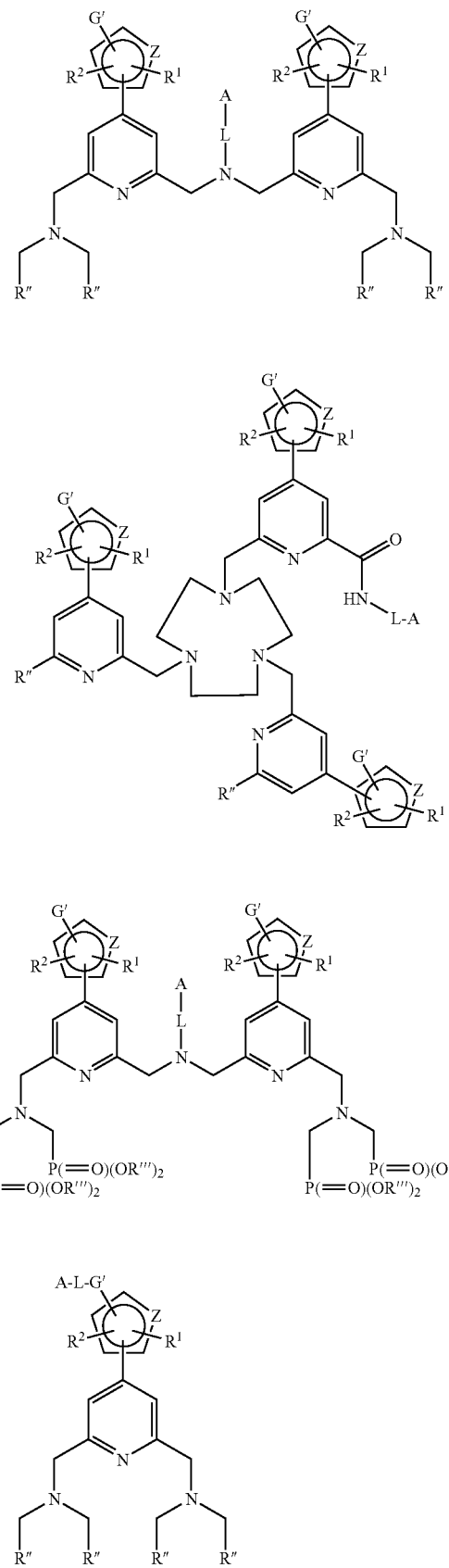
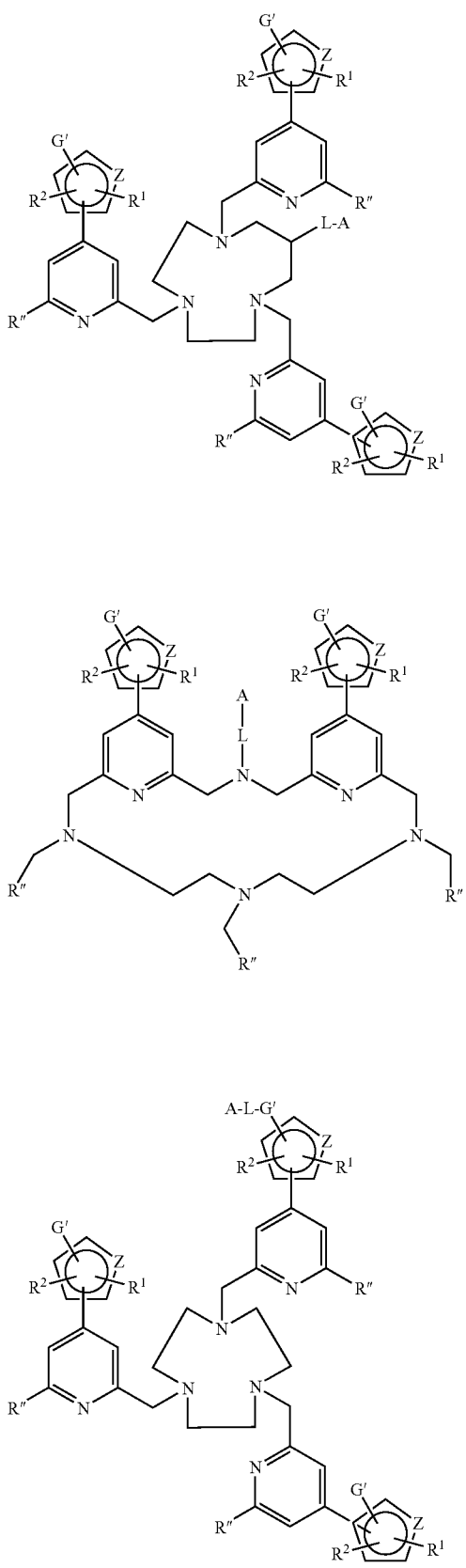

-continued acid or its salt, acid halide or an ester, R''' is an alkyl ester or an allyl ester and R'''' is an alkyl group and G' is a carboxylic or sulfonic acid ester or amide.

In a particular embodiment, the selected chelating agents are the following structures:

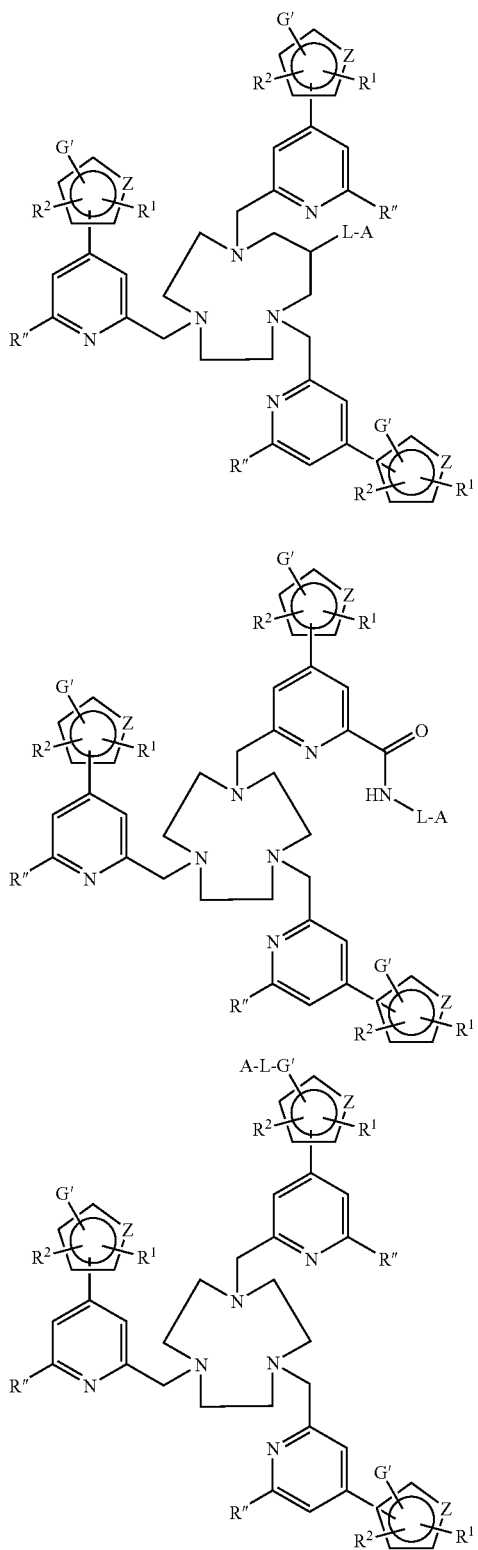

wherein $R^1$, $R^2$, L, and Z are defined as above, and A is a carboxylic acid or its salt, acid halide or an ester or an amino acid residue —CH(NHR$^3$)R$^4$ where R$^3$ is a transient protecting group and R$^4$ is a carboxylic acid or its salt, acid halide or an ester are defined as before, A is a carboxylic acid or its salt, acid halide or an ester or an amino acid residue —CH(NHR$^3$)R$^4$ where R$^3$ is a transient protecting group selected from a group consisting of Fmoc (fluorenylmethoxycarbonyl), Boc (tert-butyloxycarbonyl), or Bsmoc (1,1-dioxobenzo[b]thiophen-2-ylmethyloxycarbonyl), and R$^4$ is a carboxylic

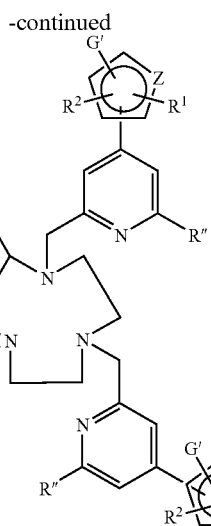

wherein $R^1$, $R^2$, L, G' and Z are defined as before, A is a carboxylic acid or its salt, acid halide or an ester or an amino acid residue —CH(NHR$^3$)R$^4$ where $R^3$ is a transient protecting group and $R^4$ is a carboxylic acid or its salt, acid halide or an ester and where $R^3$ is a transient protecting group selected from a group consisting of Fmoc (fluorenylmethoxycarbonyl), Boc (tert-butyloxycarbonyl), or Bsmoc (1,1-dioxobenzo[b]thiophen-2-ylmethyloxycarbonyl), and R" is an alkyl ester or an allyl ester of a carboxylic acid and G' is a carboxylic or sulfonic acid ester or amide.

Preferably, $R^1$ and $R^2$ are electron donating groups, L and G' are as defined above and the protecting group $R^3$ is selected from a group consisting of Fmoc, Boc, or Bsmoc, and R" is an alkyl ester or an allyl ester, and wherein Z is O or S.

The chelating agent can be introduced into biomolecules with the aid of a peptide synthesizer. The chelating agent can be coupled to an amino tethered solid support or immobilized amino acid in the presence of an activator. When the condensation step is completed the transient amino protecting group of the labeling reagent is selectively removed while the material is still attached to the solid support (e.g. with piperidine in the case of Fmoc-protecting group). Then, a second coupling of a chelating agent or other reagent (e.g. appropriately protected amino acid, steroid, hapten or organic molecule) is performed as above. When the synthesis of the desired molecule is completed, the material is detached from the solid support and deprotected. Purification can be performed by HPLC techniques. Finally, the purified ligand is converted into the corresponding lanthanide(III) chelate by the addition of a known amount of lanthanide(III) ion.

Chelating Agents for Use in Oligonucleotide Synthesis

According to another embodiment, the chelating agent according to this invention is suitable for use in the synthesis of an oligonucleotide. In this case the reactive group A is connected to the chelating agent via a linker L, and A is

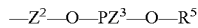
—Z$^2$—O—PZ$^3$—O—R$^5$ wherein one of the oxygen atoms optionally is replaced by sulfur, $Z^3$ is chloro or NR$^6$R$^7$, $R^5$ is a protecting group, $R^6$ and $R^7$ are alkyl groups comprising 1-8 carbons, and $Z^2$ is absent or is a radical of a purine base or a pyrimidine base or any other modified base suitable for use in the synthesis of modified oligonucleotides. Said base is connected to the oxygen atom either via i) a hydrocarbon chain, which is substituted with a protected hydroxymethyl group, or via ii) a furan ring or pyrane ring or any modified furan or pyrane ring, suitable for use in the synthesis of modified oligonucleotides.

The chelating agent can be introduced into oligonucleotides with the aid of an oligonucleotide synthesizer. A useful method is disclosed in U.S. Pat. No. 6,949,639 and EP1308452. The said patent publications disclose a method for direct attachment of a desired number of conjugate groups to the oligonucleotide structure during chain assembly. The key reaction in the synthesis strategy towards nucleosidic and acyclonucleosidic oligonucleotide building blocks is the Mitsunobu alkylation which allows introduction of various chelating agents to the acyclonucleoside or nucleoside, and finally to the oligonucleotide structure. The chelating agents are introduced during the chain assembly. Conversion to the lanthanide chelate takes place after the synthesis during the deprotection steps.

According to one embodiment $Z^2$ is a radical of any of the bases thymine, uracil, adenosine, guanine or cytosine, and said base is connected to the oxygen atom via i) a hydrocarbon chain, which is substituted with a protected hydroxymethyl group, or via ii) a furan ring having a protected hydroxymethyl group in its 4-position and optionally a hydroxyl, protected hydroxyl or modified hydroxyl group in its 2-position.

According to one embodiment the reactive group —Z$^2$—O—P(NR$^6$R$^7$)—O—R$^5$ is selected from the group consisting of:

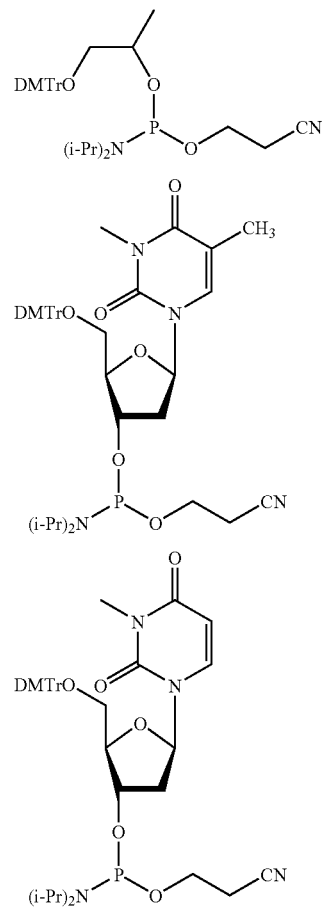

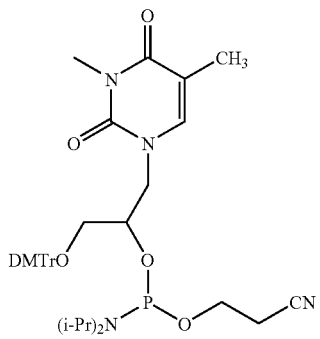
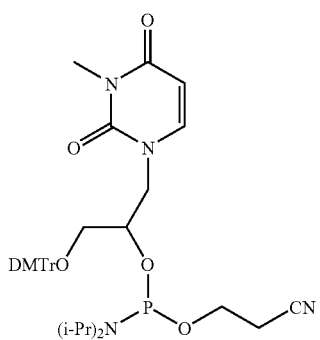
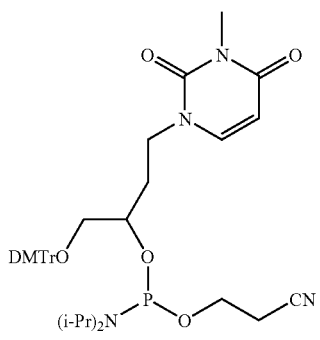
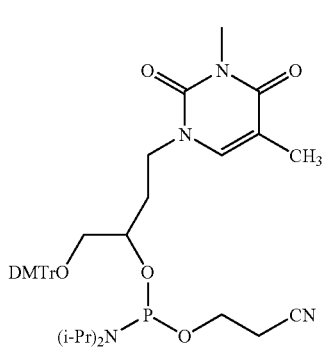
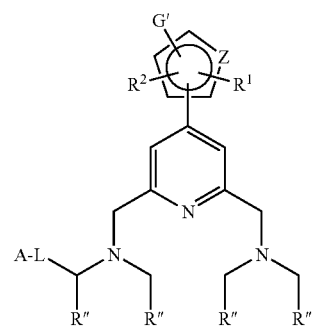
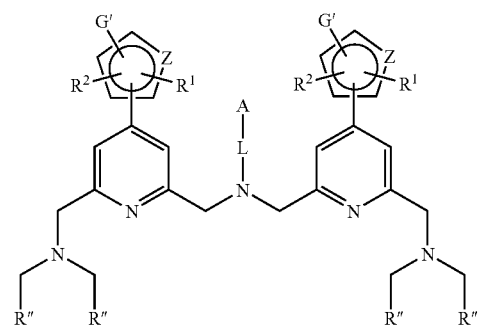
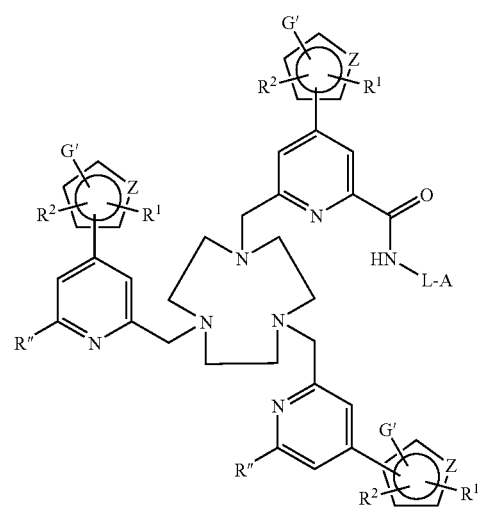
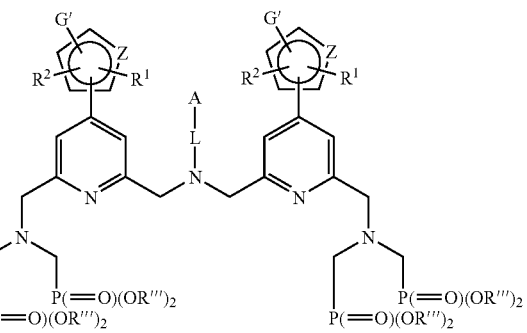
where - is the position of the linker L and DMTr is dimethoxytrityl.
According to one embodiment the chelating agent for this use is selected from one of the specific structures disclosed below

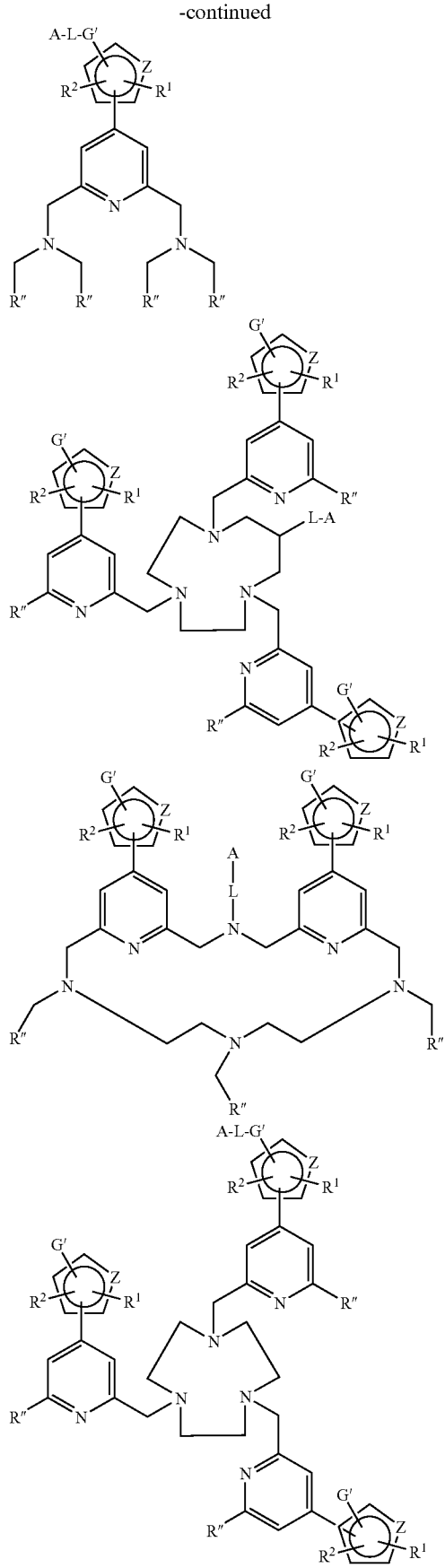
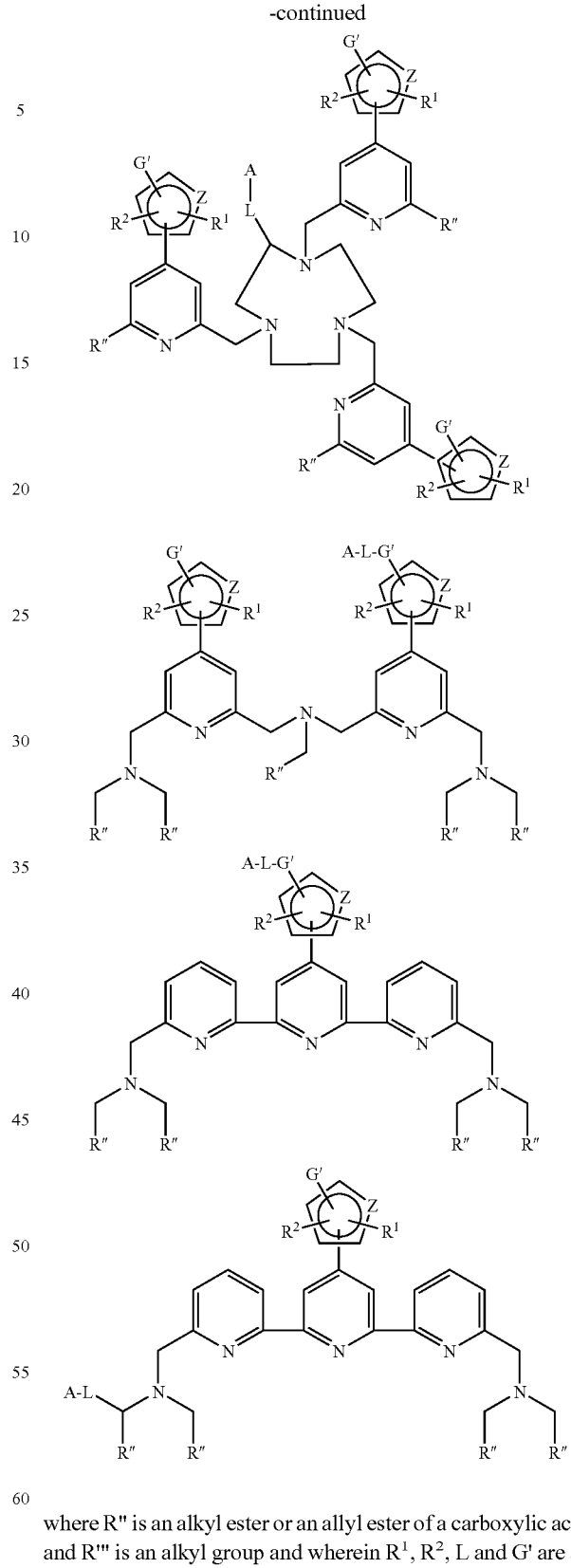
where R″ is an alkyl ester or an allyl ester of a carboxylic acid and R‴ is an alkyl group and wherein $R^1$, $R^2$, L and G′ are as defined before and A is —$Z^2$—O—P($NR^6R^7$)—O—$R^5$ as defined above.
In a particular embodiment the chelating agent is selected from the following specific structures

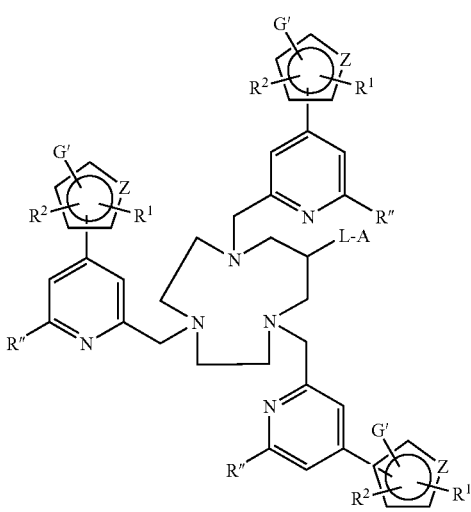

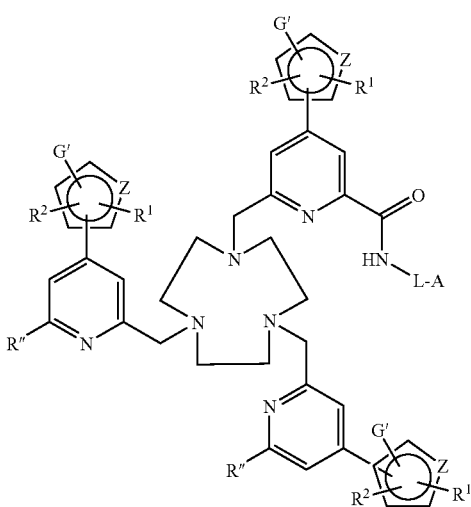

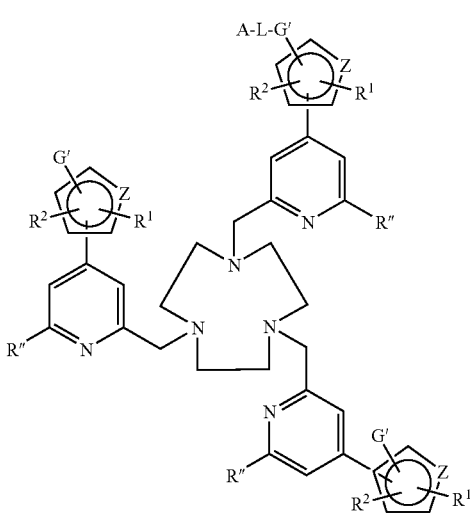

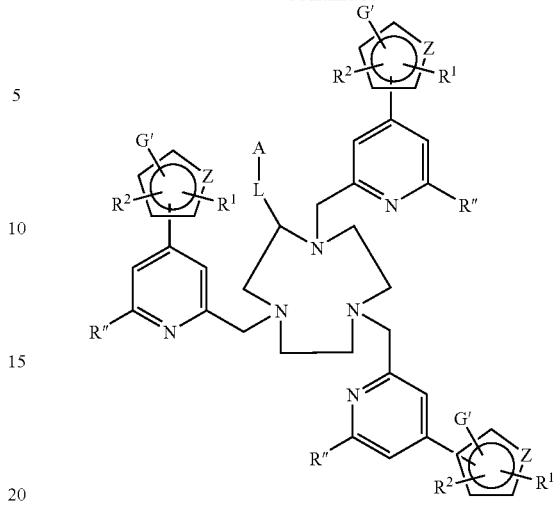

where R″ is an alkyl ester or an allyl ester or a carboxylic acid and wherein $R^1$, $R^2$, L and G′ are as defined before and A is $-Z^2-O-P(NR^6R^7)-O-R^5$ as defined above.

For the preparation of oligonucleotide conjugates tethered to a single label molecule $Z^2$ can be omitted from the structure.

Biomolecules

The biomolecule conjugated with a chelating agent or a chelate according to this invention is an oligopeptide, oligonucleotide, DNA, RNA, modified oligo- or polynucleotide, such as phosphoromonothioate, phosphorodithioate, phosphoroamidate and/or sugar- or base modified oligo- or polynucleotide, protein, oligosaccaride, polysaccaride, phospholipide, PNA, LNA, antibody, steroid, hapten, drug, receptor binding ligand and lectine.

Solid Support Conjugates

The chelates, chelating agents and biomolecules according to this invention may be conjugated on a solid support. This preferably takes place through immobilization to said solid support either covalently or noncovalently. The solid support may be a particle such as a nanoparticle or microparticle, a slide, a plate or a resin suitable for solid phase oligonucleotide or oligopeptide synthesis.

In case the chelate or chelating agent has a polymerizing group as a reactive group, then the chelate or chelating agent may be introduced in the solid support, for example a particle, simultaneously with the preparation of the particles [*Org. Biomol. Chem.*, 2006, 4, 1383]. When copper(I) catalyzed Huisgen-Sharpless reaction is used for derivatization, the chelate is tethered to an azide group and the solid support is derivatized with terminal alkynes or vice versa.

The biomolecule conjugated with the solid support, either covalently or noncovalently is a labeled oligopeptide, obtained by synthesis on a solid phase, by introduction of a chelating agent into the oligopeptide structure on an oligopeptide synthesizer, followed by deprotection and optionally introduction of a metal ion. Alternatively, the biomolecule conjugated with the solid support, either covalently or noncovalently is a labeled oligonucleotide, obtained by synthesis on a solid phase, by introduction of a chelating agent into the oligonucleotide structure on an oligonucleotide synthesizer, followed by deprotection and optionally also introduction of a metal ion. Alternatively, the biomolecule conjugated with solid support, either covalently or noncovalently is DNA, RNA, oligopeptide, oligonucleotide, polypeptide, polynucleotide or protein labeled with a chelate according to this invention.

Figure 1:
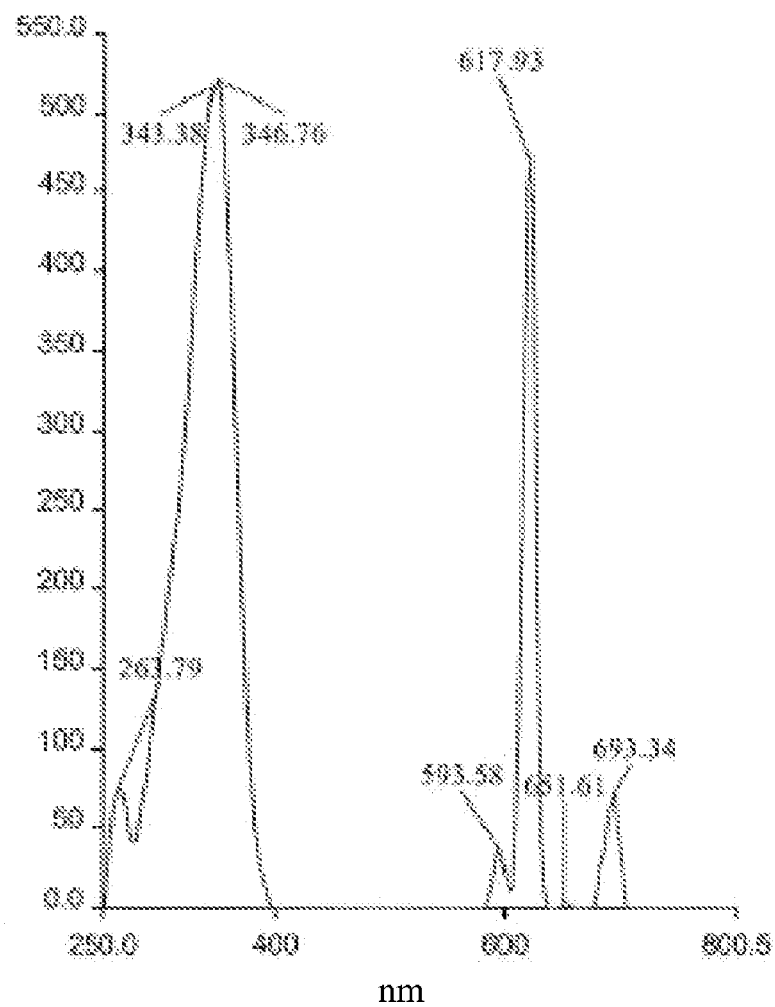
FIG. 1 demonstrates the excitation and emission spectra of the europium chelate of 6,6',6"-[(octahydro-1H-1,4,7-triazonine-1,4,7-triyl)tris(methylene)]tris[4-(4-carboxy-3,5-dimethylfuran-2-yl)pyridine-2-carboxylic acid] (14c).
Figure 2:
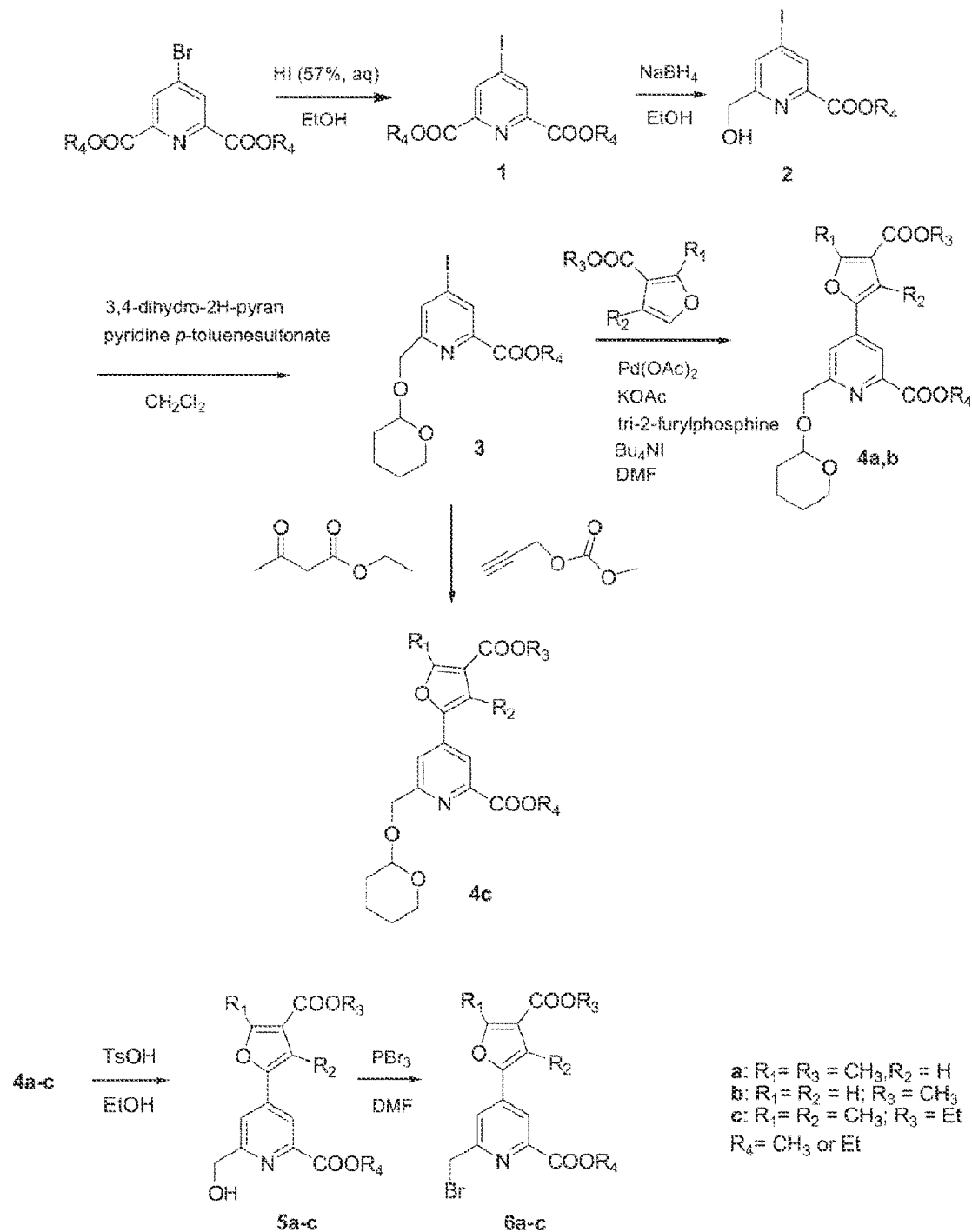
FIG. 2 demonstrates a first scheme.
Figure 3:
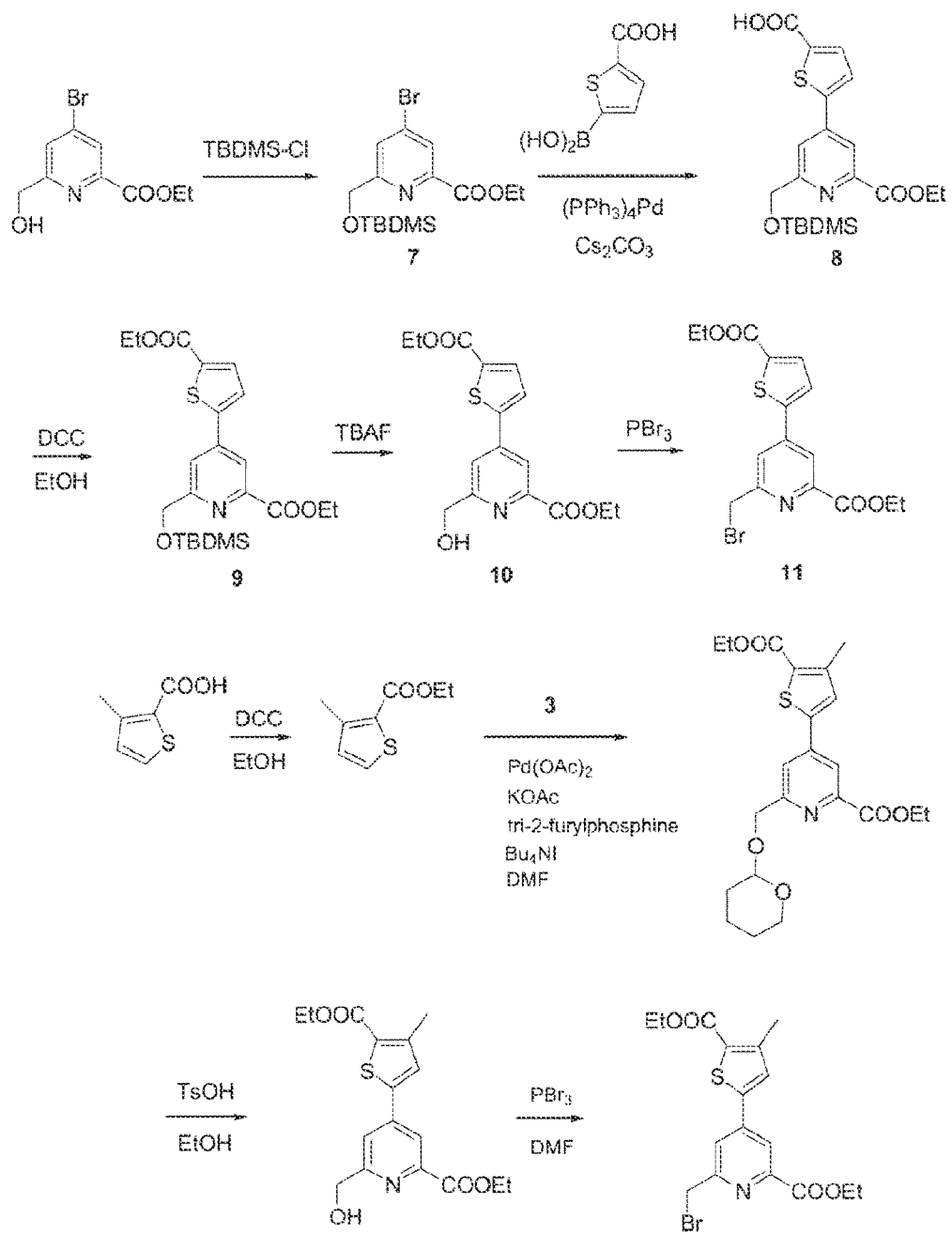
FIG. 3 demonstrates a second scheme.
Figure 4:
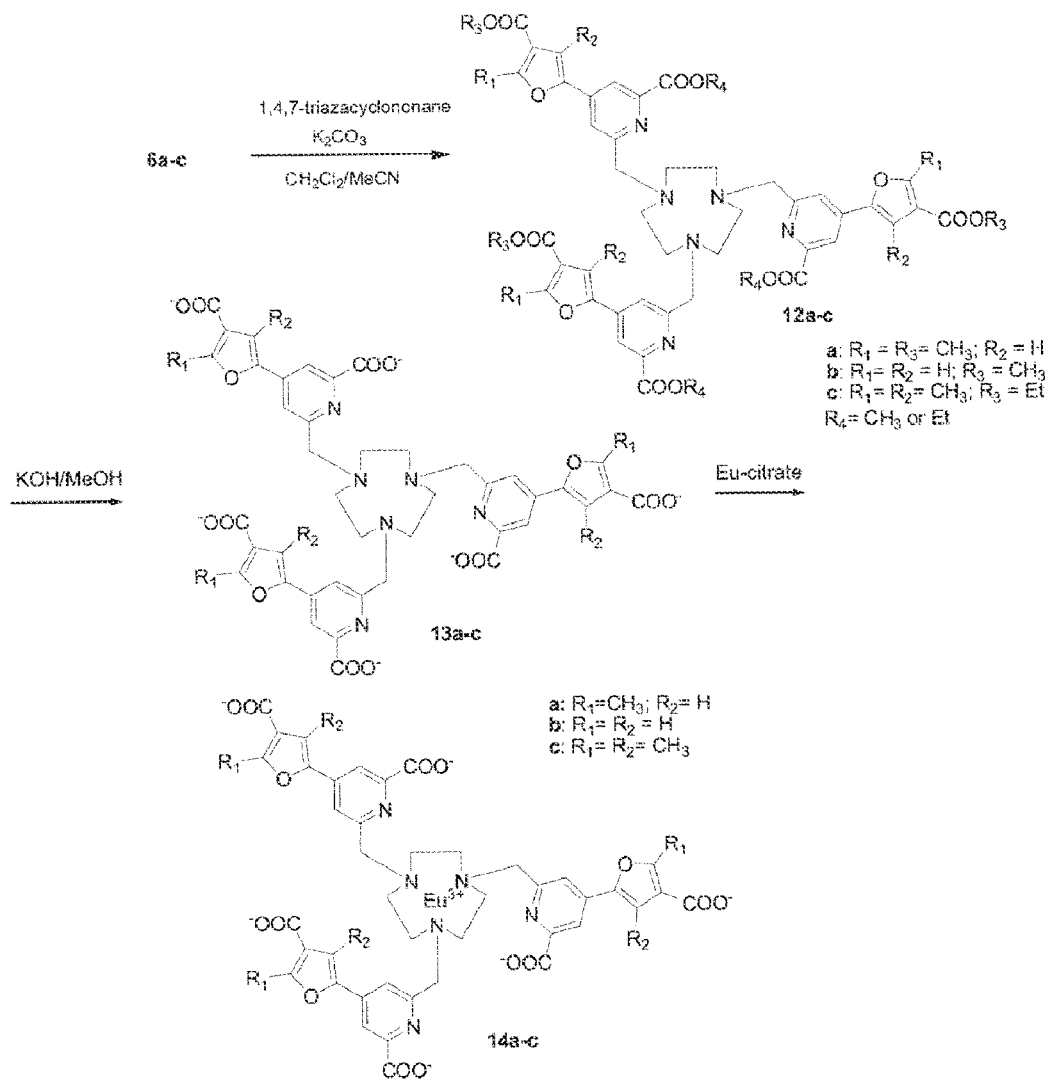
FIG. 4 demonstrates a third scheme.
Figure 5:
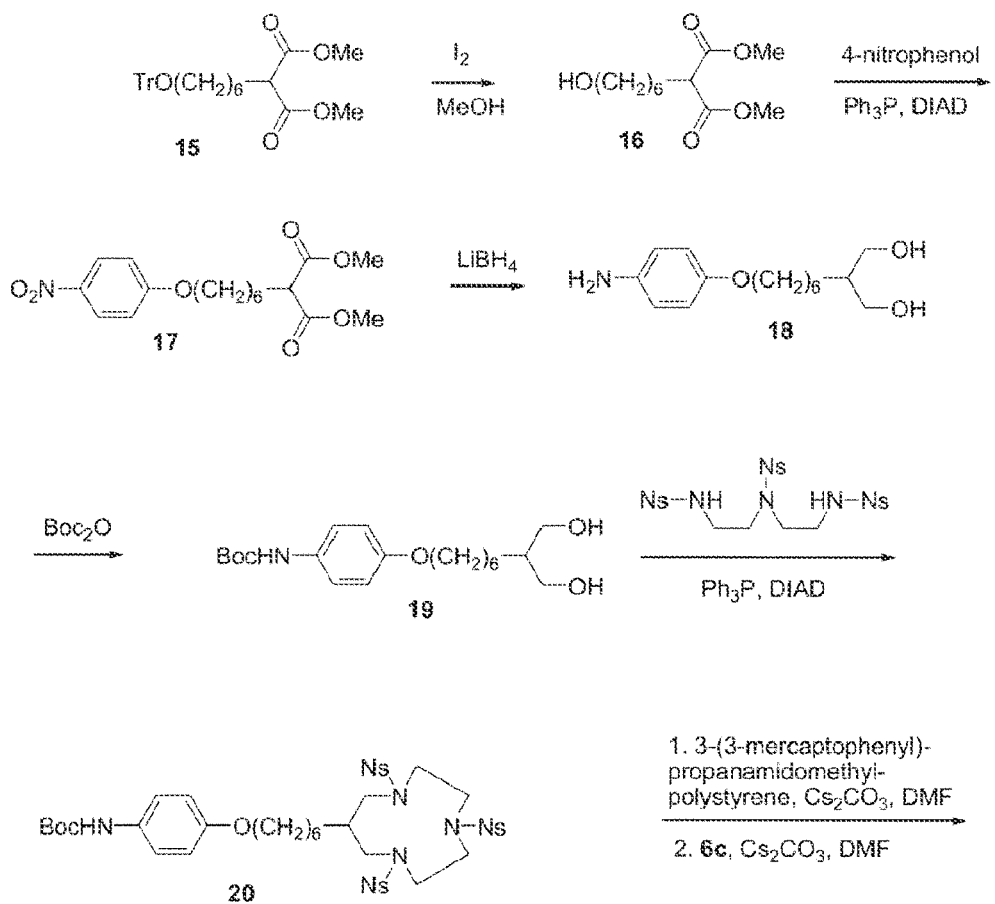
FIG. 5 demonstrates a fourth scheme.
Figure 6:
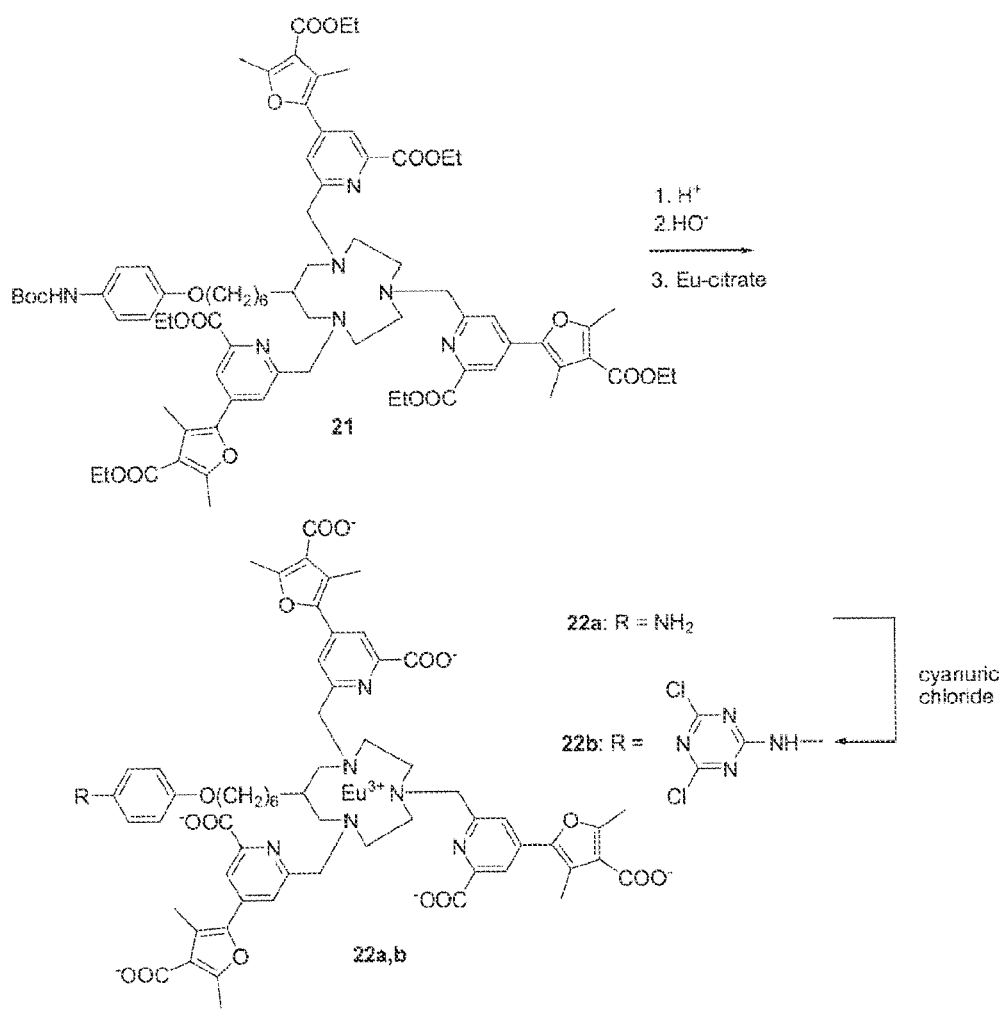
FIG. 6 demonstrates a continuation of a fourth scheme.
Figure 7:
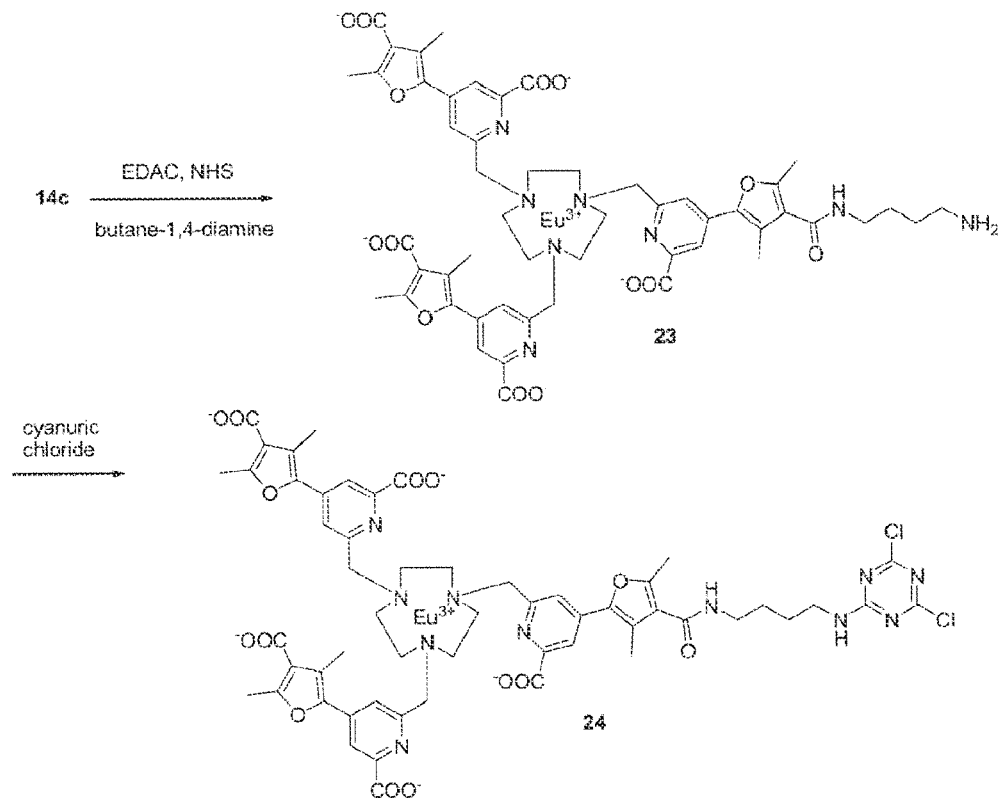
FIG. 7 demonstrates a fifth scheme.
Figure 8:
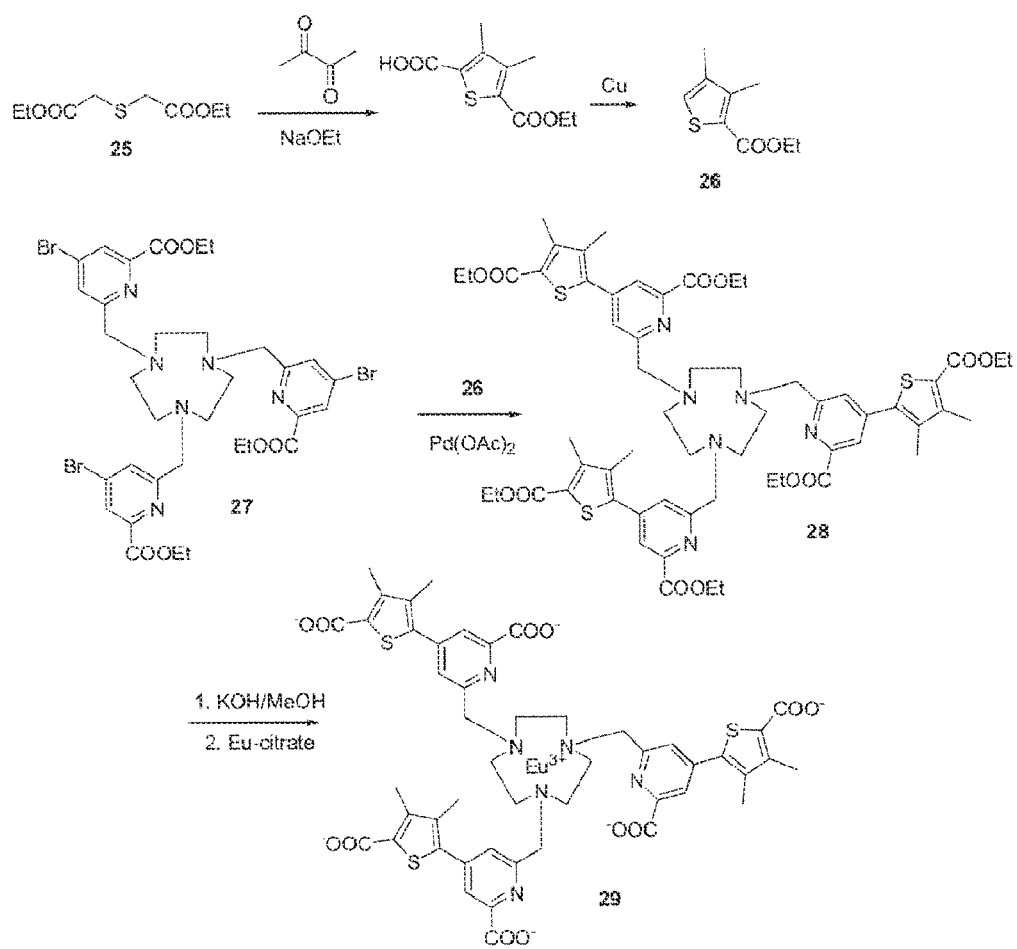
FIG. 8 demonstrates a sixth scheme.
Figure 9:
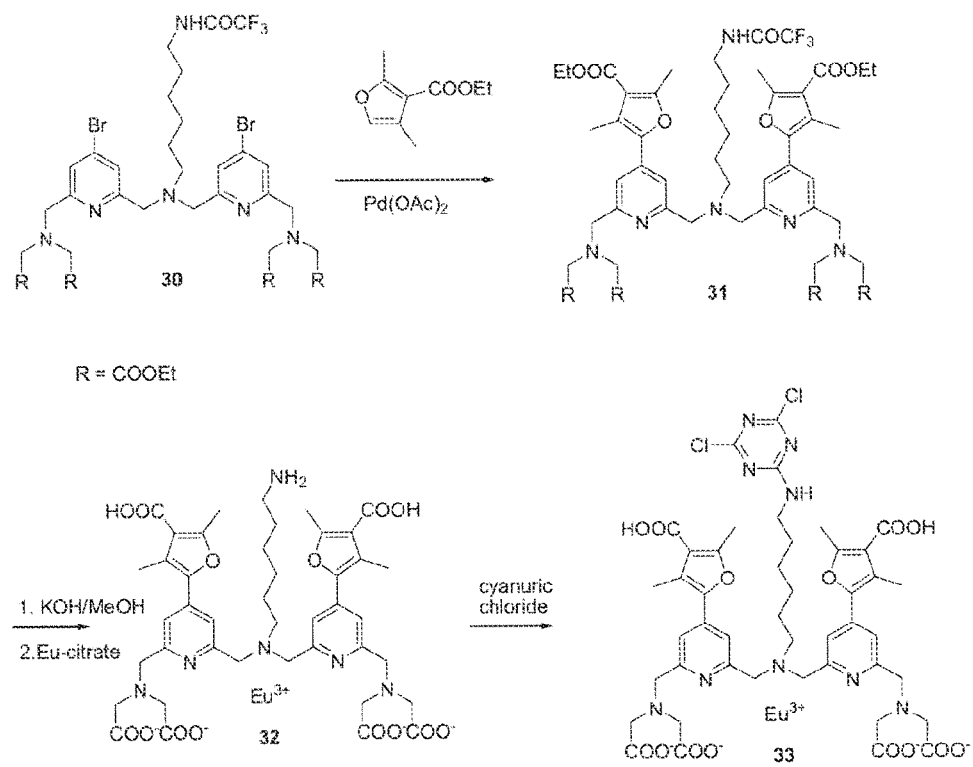
FIG. 9 demonstrates a seventh scheme.

The invention will be illuminated by the following non-restrictive examples.

EXAMPLES

The invention is further elucidated by the following examples. The structures and synthetic routes employed in the experimental part are depicted in Schemes 1-7. Schemes 1 and 2 illustrate the synthesis of the chromophores 6a-c and 11. The experimental details are given in Examples 1-17. Scheme 2 also illustrates the synthetic route for the preparation of ethyl 6-bromomethyl-4-(4'-methyl-5"-ethoxycarbonylthien-2'-yl)pyridine-2-carboxylate starting from commercially available 3-methylthiophene-2-carboxylic acid. Schemes 3-7 illustrate the synthesis of the chelates 14a-c, 22-24, 29 and 32. Experimental details are given in Examples 18-38, and 40-44.

Experimental Procedures

Adsorption column chromatography was performed on columns packed with silica gel 60 (Merck). NMR spectra were recorded either on a Brucker 250 on a Jeol LA-600 spectrometers operating at 250 and 600 MHz for $^1$H, respectively. Me$_4$Si was used as an internal reference. Coupling constants are given in Hz. Electrospray mass spectra were recorded on an Applied Biosystems Mariner ESI-TOF instrument. HPLC purifications were performed using a Shimadzu LC 10 AT instrument equipped with a diode array detector, a fraction collector and a reversed phase column (LiChrocart 125-3 Purospher RP-18e 5 µm). Mobile phase: (Buffer A): 0.02 M triethylammonium acetate (pH 7.0); (Buffer B): A in 50% (v/v) acetonitrile. Gradient: from 0 to 1 min 95% A, from 1 to 31 min from 95% A to 100% B. Flow rate was 0.6 mL min.$^{-1}$ All dry solvents were from Merck and they were used as received. Fluorescence spectra were recorded on a PerkinElmer LS-55 instrument.

Example 1

Synthesis of diethyl 4-iodopyridine-2,6-dicarboxylate (1)

A mixture of diethyl 4-bromopyridine-2,6-dicarboxylate (8.36 g, 27.7 mmol), 57% (w/w) aqueous hydriodic acid (31.05 g, 138.4 mmol) and EtOH (67 mL) was stirred at 50° C. for 1 h and neutralized with saturated NaHCO$_3$ solution. The product was extracted from the aqueous phase with CH$_2$Cl$_2$ (2×300 mL). The combined organic fractions were dried with Na$_2$SO$_4$ and evaporated to dryness. Yield was 5.24 g (54%). ESI-TOF-MS [M+H]$^+$: calc. for C$_{11}$H$_{13}$INO$_4^+$ 349.99. found 349.99.
$^1$H NMR (600 MHz, CDCl$_3$): δ 8.63 (s, 2H); 4.50 (q, J=7.2 Hz, 4H); 1.46 (t, J=7.2 Hz, 6H).

Example 2

Synthesis of ethyl 6-hydroxymethyl-4-iodopyridine-2-carboxylate (2)

Compound 1 (5.24 g, 15.0 mmol) was dissolved in EtOH (270 ml) at 40° C. NaBH$_4$ (0.57 g, 15 0 mmol) was carefully added and the mixture stirred for 40 min. The reaction was stopped by adjusting the pH to 3 with 28% (w/w) aqueous hydriodic acid. The mixture was neutralized with saturated NaHCO$_3$ solution and evaporated to dryness. The residue was suspended in water (150 mL) and the product was extracted from the aqueous phase with 10% EtOH/CH$_2$Cl$_2$ solution (3×150 ml). The combined organic fractions were dried with Na$_2$SO$_4$ and evaporated to dryness. Purification on silica gel (petroleum ether, by 40-60° C./ethyl acetate 2:5) yielded 2.89 g (63%) of the title compound.
ESI-TOF-MS [M+H]$^+$: calc. for C$_9$H$_{11}$INO$_3^+$ 307.98. found 307.98.
$^1$H NMR (600 MHz, CDCl$_3$): δ 8.37 (s, 1H); 7.95 (s, 1H); 4.83 (d, J=3.0 Hz, 2H); 4.47 (q, J=7.2 Hz, 2H); 3.29 (s, 1H); 1.44 (t, J=7.2 Hz, 3H).

Example 3

Synthesis of ethyl 6-(tetrahydropyran-2-yloxymethyl)-4-iodopyridine-2-carboxylate (3)

A mixture of 2 (2.89 g, 9.4 mmol), 3,4-dihydro-2H-pyran (1.19 g, 14.1 mmol), pyridine p-toluenesulfonate (0.236 g, 0.94 mmol) and CH$_2$Cl$_2$ (50 ml) was stirred overnight at r.t. The solvent was evaporated and the product purified on silica gel (petroleum ether, by 40-60° C./ethyl acetate 2:5), yielding 3.18 g (86%) of the title compound.
ESI-TOF-MS [M+H]$^+$: calc. for C$_{14}$H$_{19}$INO$_4^+$ 392.04. found 392.04.
$^1$H NMR (600 MHz, CDCl$_3$): δ 8.36 (d, J=1.5 Hz, 1H); 8.08 (d, J=1.5 Hz, 1H); 4.96 (d, J=14.3 Hz, 1H); 4.77 (t, J=3.6 Hz, 1H); 4.70 (d, J=14.8 Hz, 1H); 4.47 (q, J=7.2 Hz, 2H); 3.91-3.84 (m, 1H); 3.59-3.54 (m, 1H); 1.94-1.86 (m, 1H); 1.84-1.78 (m, 1H); 1.77-1.71 (m, 1H); 1.66-1.54 (m, 3H); 1.43 (t, J=7.2 Hz, 3H).

Example 4

Synthesis of ethyl 6-(tetrahydropyran-2-yloxymethyl)-4-(4'-methoxycarbonyl-5'-methylfuran-2'-yl)pyridine-2-carboxylate (4a)

A mixture of 3 (220 mg, 0.56 mmol), methyl 2-methyl-3-furancarboxylate (315 mg, 2.25 mmol), KOAc (110 mg, 1.12 mmol), tetrabutyl ammonium iodide (208 mg, 0.56 mmol), Pd(OAc)$_2$ (6.3 mg, 0.028 mmol), tri-2-furylphosphine (13.0 mg, 0.056 mmol) and dry DMF (3.8 ml) was deaerated with argon and stirred for 24 h at 120° C. After filtration and evaporation the product was purified on silica gel (5% EtOH/CH$_2$Cl$_2$+1% triethylamine), yielding 150 mg (66%) of the title compound. ESI-TOF-MS [M+H]$^+$: calc. for C$_{21}$H$_{26}$NO$_7^+$ 404.17. found 404.17.

Example 5

Synthesis of ethyl 6-(tetrahydropyran-2-yloxymethyl)-4-(4'-methoxycarbonyl-furan-2'-yl)pyridine-2-carboxylate (4b)

The title compound was synthesized as described for compound 4a in Example 4 but using methyl 3-furancarboxylate.

Example 6

Synthesis of ethyl 6-(tetrahydropyran-2-yloxymethyl)-4-(3',5'-dimethyl-4'-ethoxycarbonylfuran-2'-yl)pyridine-2-carboxylate (4c)

A mixture of 3 (3.7 g, 9.5 mmol), ethyl acetoacetate (1.2 mL, 9.5 mmol) and methylprop-2-ynylcarbonate (1.1 g, 9.5 mmol), synthesized as disclosed in *J. Org. Chem.*, 2005, 70, 6980, was dissolved in dry DMF (97 mL) and deaerated with argon. Pd(PPh$_3$)$_4$ (0.56 g, 0.48 mmol) and K$_2$CO$_3$ (2.6 g, 19 mmol) were added and the mixture was stirred overnight in the dark at 85° C. The mixture was filtered and the residue was evaporated to dryness. The residue was dissolved in CH$_2$Cl$_2$ and the solution was washed with saturated NaHCO$_3$. Purification on silica gel (petroleum ether, by 40-60° C./ethyl acetate 5:1) yielded 1.1 g (27%) of the title compound.

ESI-TOF-MS [M+H]$^+$: calc. for C$_{23}$H$_{30}$NO$_7^+$ 432.20. found 432.22.

$^1$H NMR (600 MHz, CDCl$_3$): δ 8.23 (d, J=1.2 Hz, 1H); 7.89 (s, 1H); 5.03 (d, J=14.1 Hz, 1H); 4.82 (m, 1H); 4.79 (m, 1H); 4.51 (q, J=7.1 Hz, 2H); 4.35 (q, J=7.1 Hz, 2H); 3.94-3.88 (m, 1H); 3.58-3.55 (m, 1H); 2.66 (s, 3H); 2.53 (s, 3H); 1.94-1.51 (m, 6H); 1.45 (t, J=7.0 Hz, 3H); 1.40 (t, J=7.2 Hz, 3H).

Example 7

Synthesis of ethyl 6-hydroxymethyl-4-(4'-methoxycarbonyl-5'-methylfuran-2'-yl)pyridine-2-carboxylate (5a)

A mixture of 4a (300 mg, 0.74 mmol), p-toluenesulfonic acid monohydrate (141 mg, 0.74 mmol) and EtOH (30 mL) was stirred for 4 h at r.t. The solvent was evaporated and the product purified on silica gel (5% EtOH/CH$_2$Cl$_2$+1% triethylamine), yielding 148 mg (63%) of the title compound.

ESI-TOF-MS [M+H]$^+$: calc. for C$_{16}$H$_{18}$NO$_6^+$ 320.11. found 320.13.

Example 8

Synthesis of ethyl 6-hydroxymethyl-4-(4'-methoxycarbonylfuran-2'-yl)pyridine-2-carboxylate (5b)

4b was transformed into the title compound using the method disclosed in Example 7.

Example 9

Synthesis of ethyl 4-(3',5'-dimethyl-4'-ethoxycarbonylfuran-2'-yl)-6-(hydroxymethyl)pyridine-2-carboxylate (5c)

Compound 4c (1.11 g, 2.57 mmol) was dissolved in ethanol (84 mL) and p-toluenesulfonic acid monohydrate (0.49 g, 2.57 mmol) was added. The mixture was stirred overnight at r.t. Purification on silica gel (petroleum ether, by 40-60° C./ethyl acetate/triethylamine 10:1:1→5:2:1→3:5:1) yielded 0.69 g (77%) of the title compound. ESI-TOF-MS [M+H]$^+$: calc. for C$_{18}$H$_{22}$NO$_6^+$ 348.14. found 348.15.

$^1$H NMR (600 MHz, CDCl$_3$): δ 8.23 (s, 1H); 7.69 (s, 1H); 4.89 (s, 2H); 4.49 (q, J=7.2 Hz, 2H); 4.35 (q, J=7.2 Hz, 2H); 2.65 (s, 3H); 2.53 (s, 3H); 1.46 (t, J=7.2 Hz, 3H); 1.39 (t, J=7.2 Hz, 3H).

Example 10

Synthesis of ethyl 6-(bromomethyl)-4-(4'-methoxycarbonyl-5'-methylfuran-2'-yl)pyridine-2-carboxylate (6a)

A mixture of phosphorous tribromide (125 mg, 0.46 mmol) and dry DMF was stirred at 0° C. until a white precipitate was formed. A solution of 5a (148 mg, 0.46 mmol) in a mixture of DMF (6 mL) and CH$_2$Cl$_2$ (0.2 mL) was added. The mixture was stirred for 1 h at r.t. and neutralized with saturated NaHCO$_3$ solution. The solvent was evaporated and the product purified on silica gel (petroleum ether, by 40-60° C./ethyl acetate 2:5), yielding 113 mg (64%) of the title compound.

ESI-TOF-MS [M+H]$^+$: calc. 382.02. found 382.02.

Example 11

Synthesis of ethyl 6-(bromomethyl)-4-(4'-methoxycarbonylfuran-2'-yl)pyridine-2-carboxylate (6b)

5b was transformed into the title compound using the method disclosed in Example 10.

Example 12

Synthesis of ethyl 6-(bromomethyl)-4-(3',5'-dimethyl-4'-ethoxycarbonylfuran-2'-yl)pyridine-2-carboxylate (6c)

5c was transformed into the title compound using the method disclosed in Example 10. Purified on silica gel (petroleum ether, by 40-60° C./ethyl acetate 5:1) yielded 0.28 g (36%) of the title compound.

ESI-TOF-MS [M+H]$^+$: calc. for C$_{18}$H$_{21}$BrNO$_5^+$ 410.06. found 410.06.

$^1$H NMR (600.13 MHz, CDCl$_3$): δ 8.24 (d, J=1.2 Hz, 1H); 7.85 (d, J=1.2 Hz, 1H); 4.68 (s, 2H); 4.52 (q, J=7.1 Hz, 2H); 4.35 (q, J=7.1 Hz, 2H); 2.66 (s, 3H); 2.54 (s, 3H); 1.46 (t, J=7.0 Hz, 3H); 1.40 (t, J=7.0 Hz, 3H).

Example 13

Synthesis of ethyl 6-(tert-butyldiphenylsilyloxymethyl)-4-bromopyridine-2-carboxylate (7)

Predried ethyl 6-hydroxymethyl-4-bromopyridine-2-carboxylate (1.4 g, 5 4 mmol) and imidazole (1.1 g, 6.5 mmol) were dissolved in dry DMF (1.7 mL). TBDPS-chloride (1.78 g, 6.5 mmol) was added portionwise, and the reaction was allowed to proceed for 3 h at r.t. The reaction mixture was diluted with Et$_2$O (50 mL) and washed with water and sat. NaHCO$_3$. The organic phase was dried over Na$_2$SO$_4$ and evaporated to dryness. Purification on silica gel (petroleum ether, by 40-60° C./ethyl acetate 5:2) yielded 2.5 g (92%) of the title compound.

ESI-TOF-MS [M+H]$^+$: calc. for C$_{25}$H$_{29}$BrNO$_3$Si$^+$ 520.09. found 520.06.

¹H NMR (600 MHz, CDCl₃): δ 8.14 (d, J<1 Hz, 1H); 8.04 (d, J<1 Hz, 1H); 7.66 (d, J=9.4 Hz, 4H); 7.43 (m, 2H); 7.38 (t, J=9.4 Hz, 4H); 4.93 (s, 2H); 4.44 (q, J=7.1 Hz, 2H); 1.39 (t, J=7.1 Hz, 3H); 1.15 (s, 9H).

Example 14

Synthesis of ethyl 6-(tert-butyldiphenylsilyloxymethyl)-4-(5'-carboxythien-2'-yl)-pyridine-2-carboxylate (8)

Compound 7 (0.97 g, 1.94 mmol), 5-(dihydroxyboryl)-2-thiophenecarboxylic acid (0.4 g, 2.33 mmol), Cs₂CO₃ (0.82 g, 2.52 mmol) and (PPh₃)₄Pd (45 mg, 3.88 μmol) were dissolved in dry DMF (7 mL) and deaerated with argon. The reaction was heated to 95° C. and allowed to proceed overnight. The reaction mixture was allowed to cool to r.t. and all solid materials were removed by filtration. Volatiles were removed in vacuo and the crude product was purified on silica gel (10% MeOH/CH₂Cl₂+0.1% HOAc), yielding 0.25 g (20%) of the title compound.
ESI-TOF-MS [M+H]⁺: calc. for C₃₀H₃₂NO₅SSi⁺ 546.18. found 546.61.

Example 15

Synthesis of ethyl 6-(tert-butyldimethylsilyloxymethyl)-4-(5'-ethoxycarbonylthien-2'-yl)pyridine-2-carboxylate (9)

Compound 8 (200 mg, 0.37 mmol) was dissolved in dichloromethane (200 μL). DCC (83 mg, 0.44 mmol; predissolved in 0.5 mL of THF) and a catalytic amount of DMAP were added, and the mixture was stirred for 5 min at r.t. followed by addition of dry EtOH (64 μL, 0.55 mmol). The reaction was allowed to proceed for 3 h at r.t., after which the DCU formed was filtered off and the filtrate was evaporated to dryness. Purification on silica gel (petroleum ether, by 40-60° C./ethyl acetate 5:3) yielded 73 mg (35%) the title compound.
ESI-TOF-MS [M+H]⁺: calc. for C₃₂H₃₆NO₅SSi⁺ 574.21. found 574.35.

Example 16

Synthesis of ethyl 6-hydroxymethyl-4-(5'-ethoxycarbonylthien-2'-yl)pyridine-2-carboxylate (10)

Compound 9 (70 mg, 0.12 mmol) was dissolved in dry THF (2 mL). TBAF (64 mg, 0.24 mmol) was added and the mixture was stirred for 5 h at r.t. The mixture was evaporated to dryness and purified on silica gel (5% MeOH/CH₂Cl₂), yielding 25 mg (61%) of the title compound.
ESI-TOF-MS [M+H]⁺: calc. for C₁₆H₁₈NO₅S⁺ 336.09. found 336.12.

Example 17

Synthesis of ethyl 6-bromomethyl-4-(5'-ethoxycarbonylthien-2'-yl)pyridine-2-carboxylate (11)

Compound 10 was transformed into the title compound using the method disclosed in Example 10. Purification on silica gel (5% MeOH/CH₂Cl₂) yielded 20 mg (67%) of the title compound.
ESI-TOF-MS [M+H]⁺: calc. for C₁₆H₁₇BrNO₄S⁺ 398.01. found 398.03.

Example 18

Synthesis of 1,4,7-tris{[6'-ethoxycarbonyl-4'-(4"-methoxycarbonyl-5"-methylfuran-2"-yl)pyridine-2'-yl]methyl}-1,4,7-triazacyclononane (12a)

A mixture of 6a (30 mg, 0.078 mmol), 1,4,7-triazacyclononane (3.4 mg, 0.026 mmol), K₂CO₃ (18.1 mg, 0.13 mmol), MeCN (1.2 mL) and CH₂Cl₂ (0.2 mL) was stirred overnight at r.t. The solvents were evaporated and the product purified by preparative TLC (10% EtOH/CH₂Cl₂+1% TEA), yielding 24 mg (89%) of the title compound.
ESI-TOF-MS [M+H]⁺: calc. for C₅₄H₆₁N₆O₁₅⁺ 1033.42. found 1033.42.

Example 19

Synthesis of 1,4,7-tris{[6'-ethoxycarbonyl-4'-(4"-methoxycarbonyl-furan-2"-yl)pyridine-2'-yl]methyl}-1,4,7-triazacyclononane (12b)

6b was transformed into the title compound using the method disclosed in Example 18.

Example 20

Synthesis of 1,4,7-tris{[6'-ethoxycarbonyl-4'-(3",5"-dimethyl-4"-ethoxycarbonylfuran-2"-yl)pyridine-2'-yl]methyl}-1,4,7-triazacyclononane (12c)

6c was transformed into the title compound using the method disclosed in Example 18. The product was purified by preparative TLC (petroleum ether, bp 40-60° C./ethyl acetate/triethylamine 3:5:1), yielding 30 mg (47%) of the title compound.
ESI-TOF-MS [M+H]⁺: calc. for C₅₇H₆₇N₆O₁₅⁺ 1075.47. found 1075.50.
¹H NMR (600 MHz, CDCl₃): δ 8.21 (s, 3H); 7.99 (s, 3H); 4.33 (q, J=7.1 Hz, 6H); 4.03-3.97 (m, 6H); 4.00 (s, 9H); 3.02 (bs, 8H); 2.94 (bs, 4H); 2.57 (s, 3H); 2.55 (s, 6H); 2.48 (s, 3H); 2.46 (s, 6H); 1.38 (t, J=7.0 Hz, 9H).

Example 21

Synthesis of 6,6',6"-[(octahydro-1H-1,4,7-triazonine-1,4,7-triyl)tris(methylene)]tris[4-(4-carboxy-5-methylfuran-2-yl)]pyridine-2-carboxylic acid (13a)

12a was dissolved in 0.5 M KOH/MeOH (1.6 mL) and 0.2 mL water was added. The mixture was stirred overnight at r.t. and evaporated to dryness.

Example 22

Synthesis of 6,6',6"-[(octahydro-1H-1,4,7-triazonine-1,4,7-triyl)tris(methylene)]tris[4-(4-carboxy-furan-2-yl)pyridine-2-carboxylic acid] (13b)

12b was transformed into the title compound using the method disclosed in Example 21.

Example 23

Synthesis of 6,6',6"-[(octahydro-1H-1,4,7-triazonine-1,4,7-triyl)tris(methylene)]tris[4-(4-carboxy-3,5-dimethylfuran-2-yl)pyridine-2-carboxylic acid] (13c)

12c was transformed into the title compound using the method disclosed in Example 21.

Example 24

Synthesis of 6,6',6"-[(octahydro-1H-1,4,7-triazonine-1,4,7-triyl)tris(methylene)]tris[4-(4-carboxy-5-methylfuran-2-yl)pyridine-2-carboxylic acid]europium(III) (14a)

13a (23 µmol) was dissolved in water (2 mL) and the pH was adjusted to 9 with 6 M HCl-solution. 0.2 M europium(III) citrate (0.12 mL) was added and the mixture was stirred at r.t. for 72 h. The product was precipitated by adjusting the pH to 4 with 1 M HCl-solution.

ESI-TOF-MS [M–H]$^-$: calc. for $C_{45}H_{38}EuN_6O_{15}^-$ 1055.16. found 1055.12.

Example 25

Synthesis of 6,6',6"-[(octahydro-1H-1,4,7-triazonine-1,4,7-triyl)tris(methylene)]tris[4-(4-carboxyfuran-2-yl)pyridine-2-carboxylic acid]europium(III) (14b)

13b was transformed into the title compound using the method disclosed in Example 24.

Example 26

Synthesis of 6,6',6"-[(octahydro-1H-1,4,7-triazonine-1,4,7-triyl)tris(methylene)]-tris[4-(4-carboxy-3,5-dimethylfuran-2-yl)pyridine-2-carboxylic acid]europium(III) (14c)

13c was transformed into the title compound using the method disclosed in Example 24. ESI-TOF-MS [M+Na]$^+$: calc. for $C_{48}H_{45}EuN_6NaO_{15}^+$ 1121.20. found 1121.20.

Example 27

Synthesis of methyl 2-(methoxycarbonyl)-8-(trityloxy)octanoate (15)

Sodium methoxide (1.42 g, 26.2 mmol) was dissolved in dry MeOH (90 mL). Dimethyl malonate (3.0 mL, 26.2 mmol) was added and the mixture was stirred at r.t. for one hour. (6-Bromohexyloxy)triphenylmethane (3.7 g, 8 7 mmol) was added and the mixture was refluxed overnight. The mixture was cooled to r.t. and 50 mL 10% citric acid was added. The mixture was then stirred at r.t. for 5 min. The product was extracted with $CH_2Cl_2$ (3×100 mL) and evaporated to dryness. The residue was dissolved in $CH_2Cl_2$ and dried with $Na_2SO_4$. Purification on silica gel (petroleum ether, by 40-60° C./ethyl acetate 10:1) yielded 2.3 g (56%) of the title compound. ESI-TOF-MS [M+Na]$^+$: calc. for $C_{30}H_{34}NaO_5^+$ 497.23. found 497.17.

$^1$H NMR (250 MHz, CDCl$_3$): δ 7.46-7.42 (m, 6H), 7.33-7.19 (m, 9H), 3.73 (s, 6H), 3.34 (t, J=7.6 Hz, 1H), 3.03 (t, J=6.6 Hz, 2H), 1.88 (q, J=7.2, 2H), 1.60 (quintet, 2H), 1.41-1.25 (m, 6H).

Example 28

Synthesis of methyl 8-hydroxy-2-(methoxycarbonyl)octanoate (16)

Iodine (1.0 g, 7.9 mmol) was dissolved in MeOH (100 mL). Compound 15 (4.5 g, 9.5 mmol) was added, and the mixture was stirred at 50° C. for one hour. The reaction mixture was evaporated to dryness. The residue was dissolved in $CH_2Cl_2$ and washed with 10% $Na_2SO_3$ (40 mL). The organic phase was dried with $Na_2SO_4$ and evaporated to dryness. Purification on silica gel (petroleum ether, by 40-60° C./ethyl acetate 10:1→5:3) yielded 1.96 g (89%) of the title compound.

ESI-TOF-MS [M+H]$^+$: calc. for $C_{11}H_{21}O_5^+$ 233.14. found 233.16.

Example 29

Synthesis of methyl 2-(methoxycarbonyl)-8-(4-nitrophenoxy)octanoate (17)

Compound 16 (1.92 g, 8.3 mmol), 4-nitrophenol (1.39 g, 10.0 mmol) and triphenylphosphine (2.62 g, 10.0 mmol) were dissolved in dry THF (100 mL) and deaerated with argon. Diisopropyl azodicarboxylate (2.0 mL, 10.0 mmol) was added in ten portions under argon and the mixture was stirred for 3 days at r.t. The mixture was evaporated to dryness and purified on silica gel ($CH_2Cl_2$), yielding 2.6 g (89%) of the title compound.

ESI-TOF-MS [M+H]$^+$: calc. for $C_{17}H_{24}NO_7^+$ 354.15. found 354.22.

$^1$H NMR (600 MHz, CDCl$_3$): δ 8.20 (d, 2H); 6.94 (d, 2H); 4.04 (t, J=6.4 Hz, 2H); 3.74 (s, 6H); 3.37 (t, J=7.6 Hz, 1H); 1.92 (q, J=7.6 Hz, 2H); 1.81 (quintet, J=7.0 Hz, 2H); 1.48 (quintet, 2H); 1.43-1.33 (m, 4H).

Example 30

Synthesis of 2-[6-(4-aminophenoxy)hexyl]propane-1,3-diol (18)

Compound 17 (1.19 g, 3.4 mmol) was dissolved in dry THF (50 mL). LiBH$_4$ (0.44 g, 20.2 mmol) was added and the mixture was refluxed overnight. The mixture was allowed to cool to r.t. and MeOH (10 mL) was added. The reaction mixture was stirred for 30 min at r.t. The mixture was evaporated to dryness. Saturated aqueous NaHCO$_3$ was added and the mixture was refluxed for one hour. The mixture was allowed to cool to r.t. and then filtered. The precipitate was washed with water and purified on silica gel (10% MeOH/CH$_2$Cl$_2$), yielding 0.60 g (67%) of the title compound.

ESI-TOF-MS [M+H]$^+$: calc. for $C_{15}H_{26}NO_3^+$ 268.19. found 268.20.

$^1$H NMR (600 MHz, CDCl$_3$): δ 6.63 (d, J=8.7 Hz, 2H); 6.49 (d, J=8.7 Hz, 2H); 4.56 (s, 2H); 3.79 (t, J=6.4 Hz, 2H); 3.35 (m, 4H); 1.74 (m, 1H); 1.63 (quintet, 2H); 1.37 (quintet, 2H); 1.31-1.22 (m, 6H).

Example 31

Synthesis of 2-{6-[4-(tert-butoxycarbonylamino)phenoxy]hexyl}propane-1,3-diol (19)

Compound 18 (0.55 g, 2.1 mmol) was dissolved in dry DMF. Triethylamine (0.36 mL, 2.5 mmol) and Boc anhydride (0.53 mL, 2.3 mmol) were added and the mixture was stirred at 50° C. for one hour. The mixture was evaporated to dryness. The residue was dissolved in 30% MeOH in $CH_2Cl_2$ (50 mL) and washed with saturated aqueous $NaHCO_3$. The organic phase was separated and the water phase was extracted with $CH_2Cl_2$ (2×50 mL). The organic phase was dried with $Na_2SO_4$. Purification on silica gel (30% MeOH/$CH_2Cl_2$) yielded 0.23 g (30%) of the title compound. $^1$H NMR (600 MHz, $CDCl_3$): δ 7.24 (d, 2H); 6.82 (d, 2H); 3.91 (t, J=6.4 Hz, 2H); 3.81 (d, 2H); 3.65 (t, 2H); 1.78-1.72 (m, 3H); 1.51 (s, 9H); 1.45 (quintet, 2H); 1.35 (quintet, 4H); 1.25-1.24 (m, 2H).

Example 32

Synthesis of 1,4,7-tris(2-nitrobenzenesulfonyl)-9-{6-[4-(tert-butoxycarbonyl-amino)phenoxy]hexyl}-1,4,7-triazacyclodecane (20)

Compound 19 (0.21 mg, 0.57 mmol) was dissolved in dry THF (8 mL). Triphenylphosphine and per(nosylated) diethylenetriamine (0.38 g, 0.57 mol) were added and the mixture was deaerated with argon. Diisopropyl azodicarboxylate (0.34 mL, 1.71 mmol) was added in ten portions under argon. The mixture was stirred overnight at r.t. The mixture was evaporated to dryness. The residue was dissolved in $CH_2Cl_2$ and it was washed with saturated aqueous $NaHCO_3$. The organic phase was dried with $Na_2SO_4$ and purified on silica gel ($CH_2Cl_2$), yielding 0.35 g (63%) of the title compound.

ESI-TOF-MS [M+H]$^+$: calc. for $C_{42}H_{52}N_2O_{15}S_3^+$ 990.27. found 990.27.

Example 33

Synthesis of 1,4,7-tris{[6'-(ethoxycarbonyl)-4'-(4''-ethoxycarbonyl-3'',5''-dimethylfuran-2''-yl)pyridine-2'-yl]methyl}-9-{6-[4-(tert-butoxycarbonylamino)phenoxy]hexyl}-1,4,7-triazacyclodecane (21)

Compound 20 (0.12 g, 0.12 mmol) was dissolved in dry DMF. $Cs_2CO_3$ (0.27 g, 0.84 mmol) was added and the mixture was deaerated with argon. 3-(3-mercaptophenyl)propanamidomethylpolystyrene (0.24 g, resin capacity 1.54 mmol/g) was added and the mixture was stirred for 3.5 h at r.t. An additional 0.24 g of 3-(3-mercaptophenyl)propanamidomethylpolystyrene was added and the mixture was stirred overnight at r.t. The mixture was filtrated and the residue was evaporated to dryness. 3-(3-mercaptophenyl)propanamidomethylpolystyrene (0.24 g) and $Cs_2CO_3$ (0.14 g, 0.43 mmol) were added to dry DMF (2 mL). The mixture was deaerated with argon. The nosylprotected compound was dissolved in dry DMF (2 mL) and the solution was added to the mixture of 3-(3-mercaptophenyl)propanamidomethylpolystyrene. The mixture was stirred at r.t. for 3 days. The mixture was filtrated and the filtrate was evaporated to dryness. The residue was dissolved in dry DMF (4 mL). $Cs_2CO_3$ (0.16 g, 0.49 mmol) and 6c ($R_4$=Et) (0.15 g, 0.36 mmol) was added and the mixture was stirred overnight at r.t. The reaction mixture was evaporated to dryness. The residue was dissolved in $CH_2Cl_2$ and washed with water. The organic layer was dried with $Na_2SO_4$. The product was purified by preparative TLC (10% EtOH/$CH_2Cl_2$), yielding 39 mg (23%) of the title compound.

ESI-TOF-MS [M+H]$^+$: calc. for $C_{78}H_{100}N_2O_{18}^+$ 1422.71. found 1422.73.

Example 34

Synthesis of 6,6',6''-{{9-[6-(4-aminophenoxy)hexyl]decahydro-1,4,7-triazecine-1,4,7-triyl}tris(methylene)}tris[4-(4-carboxy-3,5-dimethylfuran-2-yl)pyridine-2-carboxylic acid]europium(III) (22a)

Compound 21 (7 mg, 4.9 μmol) was dissolved in ethylacetate (700 μL) and 37% HCl (300 μL) was added. The mixture was stirred at r.t. for 2 hours. The mixture was evaporated to dryness. The residue was dissolved in 0.5 M KOH/MeOH (1 mL). 10 M KOH in water (100 μL) was added and the solution was stirred at r.t. for 3 days. Methanol was removed from the reaction mixture in vacuo and the pH was adjusted to 8 with 1 M HCl. 0.2 M europium(III) citrate (30 μL) was added and the mixture was stirred overnight at r.t. The product was purified by HPLC.

ESI-TOF-MS [M−2H]$^{2-}$: calc. for $C_{61}H_{62}EuN_7O_{16}^{2-}$ 650.67. found 650.71.

Example 35

Synthesis of 6,6',6''-{{9-{6-[4-(4,6-dichloro-1,3,5-triazinylamino)phenoxy]hexyl}decahydro-1,4,7-triazecine-1,4,7-triyl}tris(methylene)}tris[4-(4-carboxy-3,5-dimethylfuran-2-yl)pyridine-2-carboxylic acid]europium(III) (22b)

Compound 22a (2.5 mg, 1.7 μmol) was dissolved in 1 mL of 0.1 M $CH_3COONa$ (pH 6.5). Cyanuric chloride (0.4 mg, 2.1 μmol) was dissolved in acetone (1 mL) and 0.3 mL water was added. The solutions were combined, the pH was adjusted to 6.5 with 0.1 M NaOH-solution and the mixture was stirred at r.t. for 2 hours. The product was precipitated by adjusting the pH to 4 with 1 M HCl. The precipitate was washed twice with acetone and dried in a vacuum desiccator.

ESI-TOF-MS [M−2H]$^{2-}$: calc. for $C_{64}H_{61}Cl_2EuN_{10}O_{16}^{2-}$ 724.14. found 724.09.

Example 36

Synthesis of 2-{4,7-bis{[4-(4-carboxy-3,5-dimethylfuran-2-yl)]-6-carboxypyridin-2-ylmethyl}-1,4,7-triazacyclononan-1-ylmethyl}-4-[4-(4-aminobutyl)aminocarbonyl-3,5-dimethylfuran-2-yl]pyridine-2-carboxylic acid europium(III) 23

A mixture of compound 14c (5 μmol), 1,4-diaminobutane (0.45 mg, 5 μmol), EDAC (1.1 mg, 5.5 μmol) and N-hydroxysuccinimide (0.5 mg) in 1.2 mL of DMF/water (4:1) was stirred overnight at r.t. The product was purified by HPLC. ESI-TOF-MS [M+2H]$^{2+}$: calc. 585.16. found 585.17.

Example 37

Synthesis of 2-{4,7-bis{[4-(4-carboxy-3,5-dimethylfuran-2-yl)]-6-carboxypyridin-2-ylmethyl}-1,4,7-triazacyclononan-1-ylmethyl}-4-{4-[4-(4,6-dichloro-1,3,5-triazinyl)aminobutyl]aminocarbonyl-3,5-dimethylfuran-2-yl}pyridine-2-carboxylic acid europium(III) 24

Compound 23 (4.5 mg, 3.9 μmol) was dissolved in 1 mL of 0.1M $CH_3COONa$ (pH 6.5). Cyanuric chloride (0.8 mg, 4.2 mmol) was dissolved in acetone (1 mL) and 0.3 mL water was added. The solutions were combined, the pH was adjusted to 6.5 with 0.1 M NaOH-solution and the mixture was stirred for 20 min at r.t. The product was precipitated by adjusting the pH to 3 with 1 M HCl. The precipitate was washed twice with 2 mL of acetone and dried in a vacuum desiccator.

ESI-TOF-MS calc. for $C_{20}H_{15}EuN_3O_{10}S^-$ 643.99. found 643.40.

Example 38

Labeling of PT66 Antiphosphotyrosine with the Chelate 24

To an aqueous solution of compound 24 (100 mM, in aq. $NaHCO_3$, pH 8.3) the antibody (0.8 mg) was added, and the pH was adjusted to 9.3 with $NaHCO_3$. The reaction was allowed to proceed overnight in the dark at 4° C. The labeled antibody was initially purified on a Centricon30 funnel (4500 rpm for 30 min using 50 mM TSA as the eluent (4×1 mL)) followed by column chromatography on Sephadex G50 DNA grade (50 cm×1 cm) using 50 mM TSA as the eluent. Fractions containing the desired product (as judged by fluorescence spectrometry) were pooled and filtered through a 0.2 μm filter.

Example 39

The Kinase Assay

The positive control (2 nM Eu-labeled PT66 and 10 mM phosphorylated peptide; Biotinyl-ε-aminocaproyl-Glu-Pro-Gln-Tyr($PO_3H_2$)-Glu-Glu-Ile-Pro-Ile-Tyr-Leu-OH: Bachem) and the negative control (2 nM Eu-labeled PT66+20 nM SA-Alexa647; 4.3 Alexa/SA) were incubated for 30 min at r.t. The measurement was performed on a Victor 3 multi-label counter (PerkinElmer LAS) using a 50 μs delay/100 μs TR window at 665 nm and 615 nm for the energy transfer signal and the europium signal, respectively.

| Energy transfer signal at 665 nm | | | |
|---|---|---|---|
| chelate/IgG | Avg Pos | Avg Neg | S/B |
| 1.3 | 20108 | 700 | 28.7 |
| 2.0 | 27951 | 974 | 28.7 |
| 2.6 | 35871 | 1115 | 32.2 |
| 3.2 | 33960 | 1200 | 28.3 |

| Eu signal at 615 nm | | | |
|---|---|---|---|
| chelate/IgG | Avg Pos | Avg Neg | E |
| 1.3 | 154487 | 208766 | 0.26 |
| 2.0 | 237086 | 311151 | 0.24 |
| 2.6 | 273813 | 362397 | 0.24 |
| 3.2 | 291881 | 385378 | 0.24 |

Example 40

The synthesis of ethyl 3,4-dimethylthiophene-2-carboxylate, 26

The title compound was prepared using the methods disclosed in U.S. Pat. No. 6,559,993 and US 2004/0147765. Accordingly, the thioether 25 (10.8, 52.4 mmol) and 2,3-butanedione (2.25 g, 26.2 mmol) were dissolved in dry THF (20 mL) under argon. A solution of NaOEt in ethanol (20%, m/v; 1.5 eq) was added dropwise, and the mixture was heated at 65° C. for 2.5 h and cooled to rt. After aqueous work up the product was dried over $Na_2SO_4$ and purified on silica gel to give of 2.5 g of 5-(ethoxycarbonyl)-3,4-dimethylthiophene-2-carboxylic acid, which was dissolved in chinoline. Copper (0.30 g) was added, and the mixture was aerated for 30 min at rt followed by heating overnight at 140° C. After aqueous work up the product was dried and purified on silica gel. Compound 26: $^1$H NMR ($CDCl_3$): δ 7.08 (1H, s); 4.33 (2H, q, J 7.2); 2.47 (3H, s); 2.18 (3H, s); 1.38 (3H, t, J 7.2). ESI-TOF-MS $[M+H]^+$: calc. for $C_9H_{13}O_2S^+$ 185.06. found 185.07.

Example 41

The synthesis of 1,4,7-tris{[6'-methoxycarbonyl-4'-(4"-ethoxycarbonyl-3",5"-dimethylthiophen-2"-yl)pyridine-2'-yl]methyl}-1,4,7-triazacyclononane (28)

A mixture of compound 27 (0.1 mmol), compound 26 (3.0 mmol), palladium acetate (0.15 mmol), trifurylphosphine (0.30 mmol), potassium acetate (0.6 mmol), tetabutylammonium iodide (0.3 mmol) and DMF (5 mL) was deaerated with argon and stirred overnight in dark at 100° C. The reaction mixture was filtered, evaporated to dryness and the product was purified on a preparative TLC plate coated with silica gel. ESI-TOF-MS $[M+H]^+$: calc. for $C_{56}H_{64}N_6O_{12}S_3^+$, 1207.49. found 1207.50.

Example 42

Synthesis of 6,6',6"-[(octahydro-1H-1,4,7-triazonine-1,4,7-triyl)tris(methylene)]-tris[4-(4-carboxy-3,5-dimethylthiophen-2-yl)pyridine-2-carboxylic acid] europium(III) (29)

Compound 28 was transformed into the title compound using the method disclosed in Example 24. ESI-TOF-MS $[M-2H]^{2-}$ calc. for $C_{48}H_{43}EuN_6O_{12}S_3^{2-}$ 572.07. found 572.02.

Example 43

Synthesis of 2,2',2",2'''-{[6-(trifluoroacetamidoaminohexyl)]bis(methylene)bis 4-[(4"-ethoxycarbonyl-3",5"-dimethylfuran-2"-yl)pyridine-6,2-diyl)]bis(methylenenitrilo)}tetrakis(acetic acid)tetra(ethyl ester) 31

Reaction between compound 30, and ethyl 2,4-dimethylfuran-3-carboxylate using the method described in Example 41 yielded the title compound.

Example 44

Synthesis of 2,2',2",2'''-{[6-aminohexylimino]bis(methylene)bis[4-(4"-carboxy-3",5"-dimethylfuran-2"-yl)]pyridine-6,2-diyl-)]bis(methylenenitrilo)}tetrakis(acetic acid)europium(III), 32

Compound 31 was transformed into the title compound using the method disclosed in Example 21. ESI-TOF-MS calc. for $C_{42}H_{48}EuN_6O_{14}^-$ 1013.24. found 1013.25.

Synthesis of 2,2',2",2"'-{[6-(4,6-dichloro-1,3,5-triazinyl)aminohexylimino]bis(methylene)bis[4-(4"-carboxy-3",5"-dimethylfuran-2"-yl)]pyridine-6,2-diyl-)bis(methylenenitrilo)}tetrakis(acetic acid) europium(III), 33

Compound 32 was converted to the title compound using the method described in Example 37. ESI-TOF-MS [M–H]⁻ calc. for $C_{45}H_{47}Cl_2EuN_9O_{14}^-$ 1160.18. found 1160.25.

Photophysical properties of certain chelates according to this invention are shown in Table 1. The photophysical properties of the chelates were determined by measuring the excitation and emission spectra and fluorescence lifetime in TS buffer (50 mM tris, 150 mM NaCl, pH 7.75) with LS-55 luminescence spectrometer (PerkinElmer Instruments, Connecticut, USA). Measurements were done with appropriate concentrations depending on expected fluorescence intensity.

TABLE 1

Photophysical properties of the chelates synthesized

| Compound | Excitation maxima/nm | Emission wavelenght/nm |
|---|---|---|
| a) | 328 | 618 |
| 14b | 330 | 617 |
| 14a | 338 | 618 |
| 14c | 347 | 618 |
| b) | 316 | 616 |
| c) | 317 | 616 |
| 29 | 339 | 616 |
| d) | 312 | 616 |
| 32 | 330 | 615 | a) 6,6',6"-[(octahydro-1H-1,4,7-triazonine-1,4,7-triyl)tris(methylene)]-tris[(furan-2-yl)pyridine-2-carboxylic acid] europium(III), synthesized as disclosed in WO2005/021538
b) 2,2',2",2"'-{[4-(thien-2'-yl)pyridine-2,6-diyl]bis(methylenenitrilo)}-tetrakis(acetic acid) europium(III), synthesized as disclosed in Latva et al. *J. Luminescence*, 1997, 35, 149.
c) 2,2',2",2"'-{[4-(fur-2'-yl)pyridine-2,6-diyl]bis(methylenenitrilo)}tetrakis-(acetic acid) europium(III), synthesized as disclosed in WO2005/021538.
d) 2,2',2",2"'-{[6-aminohexylimino]bis(methylene)bis[4-(2-furyl)pyridine-6,2-diyl]}bis(methylenenitrilo)}tetrakis(acetic acid) europium (III), synthesized as disclosed in WO2005/021538.

It will be appreciated that the methods of the present invention can be incorporated in the form of a variety of embodiments, only a few of which are disclosed herein. Although the examples are mainly given for the furyl derivatives, the same synthetic procedures are applicable to the corresponding thienyl derivatives as well.

Although only the synthesis of europium(III) chelates is presented here, it is clear that an artisan can prepare the corresponding samarium(III), terbium(III) and dysprosium (III) chelates using the methods disclosed here by substituting the europium(III) salt by the desired lanthanide(III) salt. It will be apparent for an expert skilled in the field that other embodiments exist and do not depart from the spirit of the invention. Thus, the described embodiments are illustrative and should not be construed as restrictive.

The invention claimed is:

1. A chelate comprising
a lanthanide ion, $Ln^{3+}$, selected from $Eu^{3+}$, $Sm^{3+}$, $Tb^{3+}$ and $Dy^{3+}$,
a chromophoric moiety,
a chelating part comprising at least two carboxylic acid or phosphonic acid groups, or esters, amides or salts of said acids, attached to an aromatic unit of the chromophoric moiety, either directly or via a cyclic or acyclic N-containing hydrocarbon chain,
a reactive group A, tethered to the chromophoric moiety or to the chelating part either directly or via a linker L, the reactive group A enabling binding to a biomolecule or to a functional group on a solid phase, wherein i) the reactive group A is selected from the group consisting of isothiocyanate, bromoacetamido, iodoacetamido, maleimido, 4,6-dichloro-1,3,5-triazin-2-ylamino, pyridyldithio, thioester, aminooxy, azide, hydrazide, amino, alkyne, a methacroyl group, and a carboxylic acid or acid halide or an active ester thereof or

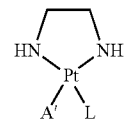

wherein A' is a cleaving ligand selected from Cl, $(CH_3)_2SO$, $H_2O$, and $NO_3$, and wherein -L is the position of linker L, ii) the linker L is formed from one to ten moieties, each moiety being selected from the group consisting of phenylene, alkylene containing 1-12 carbon atoms, ethynydiyl (—C≡C—), ethylenediyl (—C=C—), ether (—O—), thioether (—S—), amide (—CO—NH—, —CO—NR'—, —NH—CO— and —NR'—CO—), carbonyl (—CO—), ester (—COO— and —OOC—), disulfide (—SS—), sulfonamide (—SO₂—NH—, —SO₂—NR'—), sulfone (—SO₂—), phosphate (—O—PO₂—O—), diaza (—N=N—), and tertiary amine, wherein R' represents an alkyl group containing less than 5 carbon atoms, iii) the chromophoric moiety comprises one or more aromatic units, wherein at least one of the aromatic units is a furyl or thienyl substituted pyridyl group, wherein the furyl or thienyl group is substituted with one or more, same or different, electron donating groups selected from methyl, ethyl, n-propyl, i-propyl, n-butyl, t-butyl, sec-butyl, methoxy, ethoxy, n-propoxy, i-propoxy, n-butoxy, t-butoxy and sec-butoxy, and optionally with a carboxylic or sulfonic acid group, or with an ester, an amide or a salt of said acids, G, and wherein the aromatic units are tethered directly to each other to form a terpyridyl group, or are tethered to each other via a cyclic or an acyclic N-containing hydrocarbon chain.

2. A chelate according to claim 1, selected from the group consisting of;

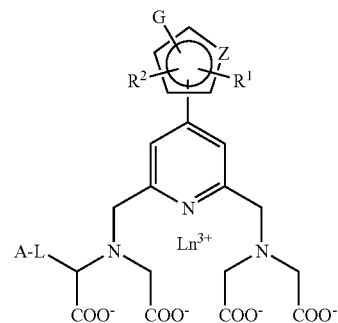

39
-continued
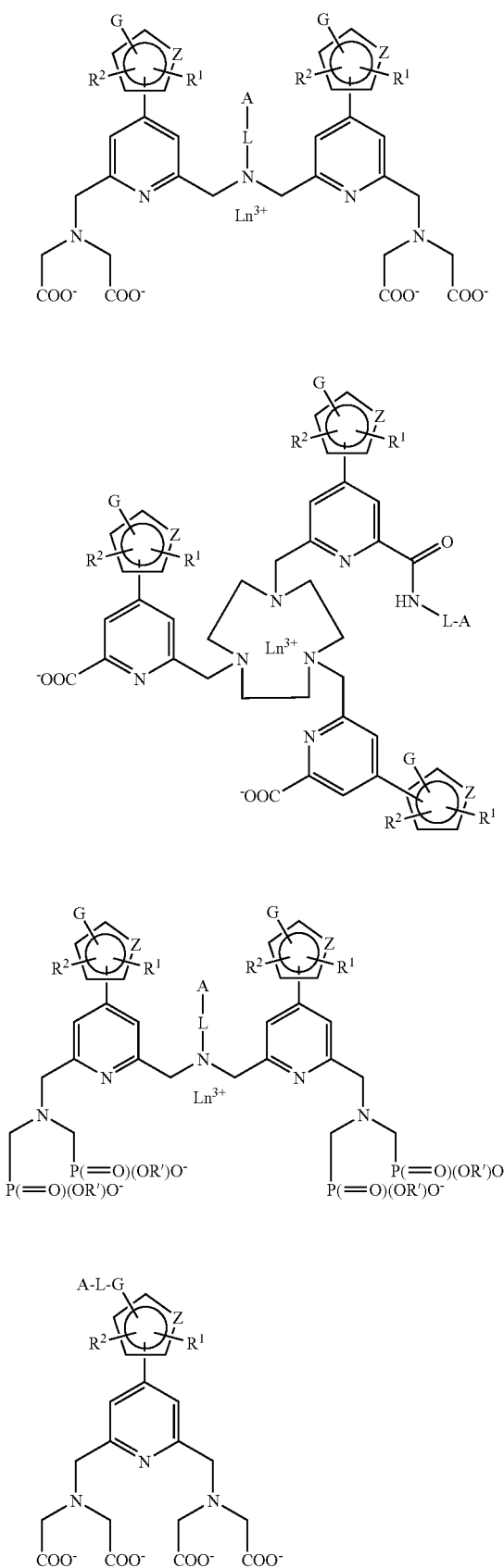
40
-continued
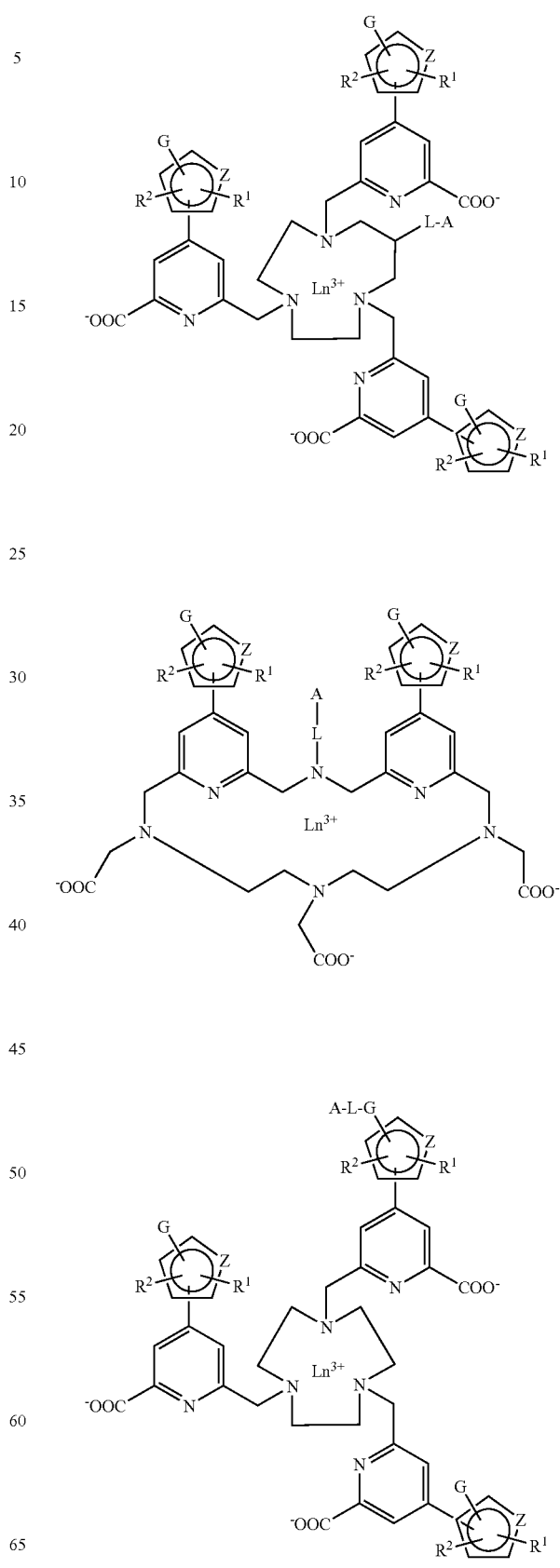

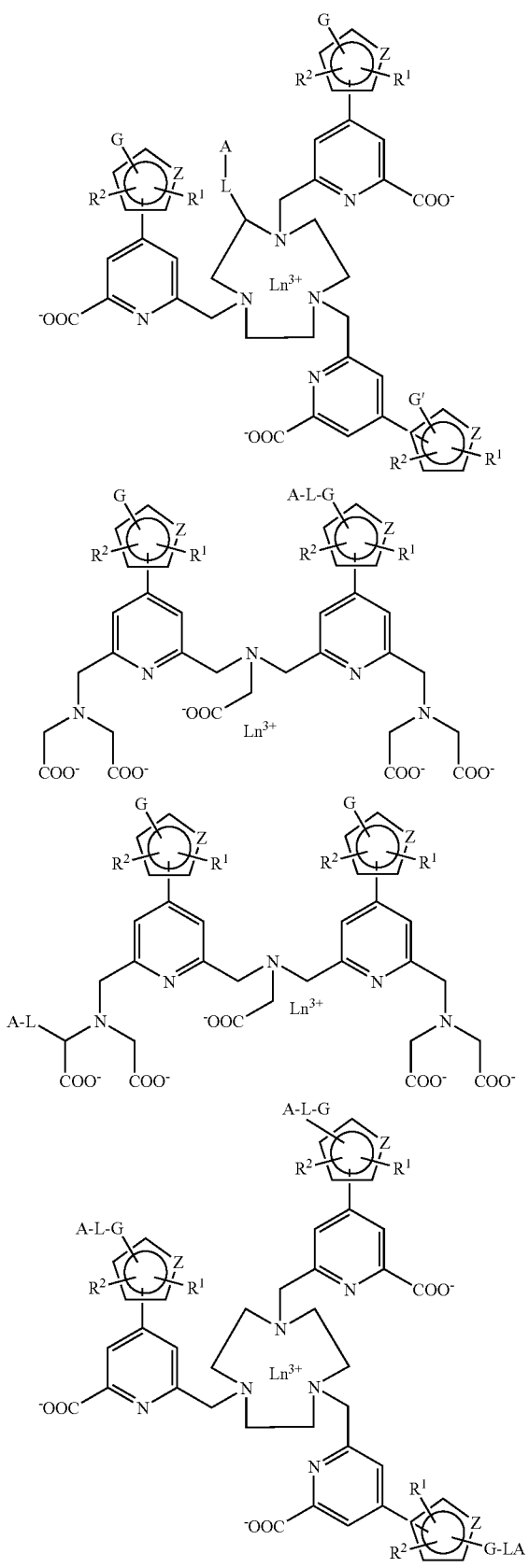

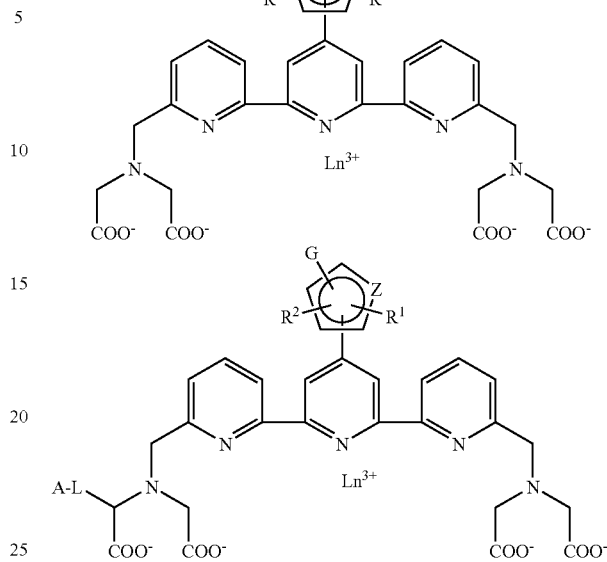

wherein $R^1$ and $R^2$ are electron donating groups, L, G, R' and A are defined as in claim 1, and Z is either O or S for furyl and thienyl, respectively.

3. A chelating agent comprising;
a chromophoric moiety,
a chelating part comprising at least two carboxylic acid or phosphonic acid esters or amides of said acids, attached to an aromatic unit of the chromophoric moiety, either directly or via a cyclic or acyclic N-containing hydrocarbon chain,
a reactive group A, tethered to the chromophoric moiety or to the chelating part either directly or via a linker L, said reactive group A enabling binding to a biomolecule or to a functional group on a solid phase, wherein
i) the reactive group A is a carboxylic acid or its salt, acid halide or an ester or an amino acid residue —CH(NHR$^3$)R$^4$, where $R^3$ is a transient protecting group and $R^4$ is a carboxylic acid or its salt, acid halide or ester,
ii) the linker L is formed from one to ten moieties, each moiety being selected from the group consisting of phenylene, alkylene containing 1-12 carbon atoms, ethynydiyl (—C≡C—), ethylenediyl (—C═C—), ether (—O—), thioether (—S—), amide (—CO—NH—, —CO—NR'—, —NH—CO— and —NR'—CO—), carbonyl (—CO—), ester (—COO— and —OOC—), disulfide (—SS—), sulfonamide (—SO$_2$—NH—, —SO$_2$—NR'—), sulfone (—SO$_2$—), phosphate (—O—PO$_2$—O—), diaza (—N═N—), and tertiary amine, wherein R' represents an alkyl group containing less than 5 carbon atoms,
iii) the chromophoric moiety comprises one or more aromatic units, wherein at least one of the aromatic units is a furyl or thienyl substituted pyridyl group, wherein the furyl or thienyl group is substituted with one or more, same or different, electron donating groups selected from methyl, ethyl, n-propyl, i-propyl, n-butyl, t-butyl, sec-butyl, methoxy, ethoxy, n-propoxy, i-propoxy, n-butoxy, t-butoxy and sec-butoxy, and optionally with a carboxylic or sulfonic acid ester or amide of said acids, G', and wherein the chromophoric moieties are tethered directly to each other to form a terpyridyl group, or are tethered to each other via a cyclic or acyclic N-containing hydrocarbon chain.
4. A chelating agent according to claim 3, selected from the group consisting of;
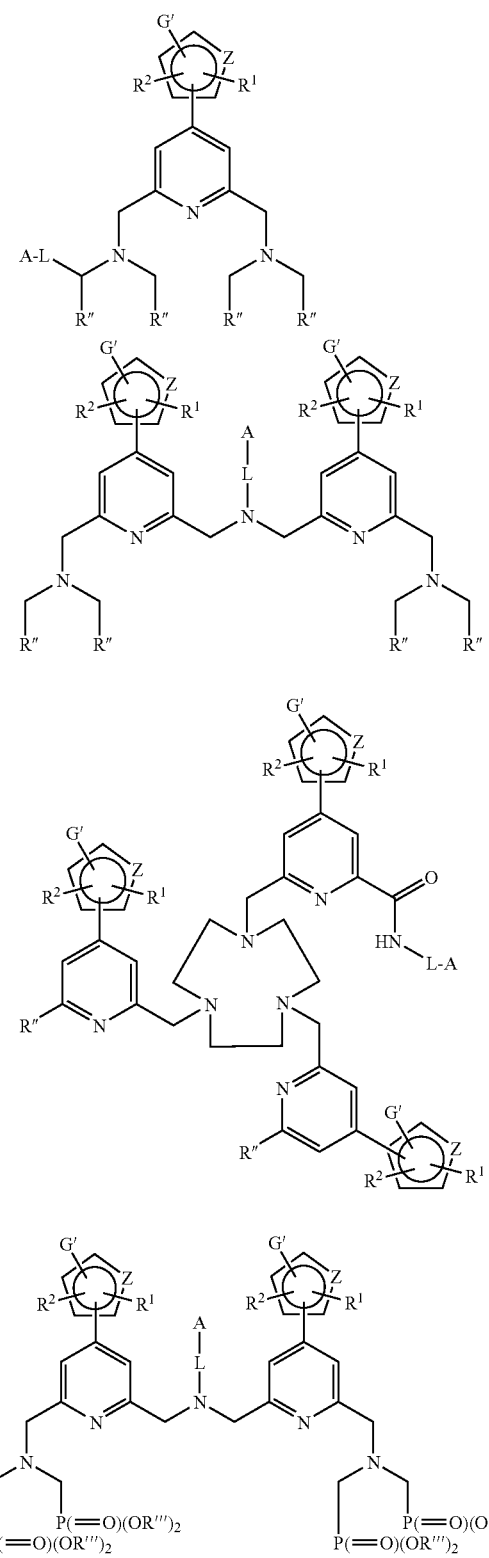
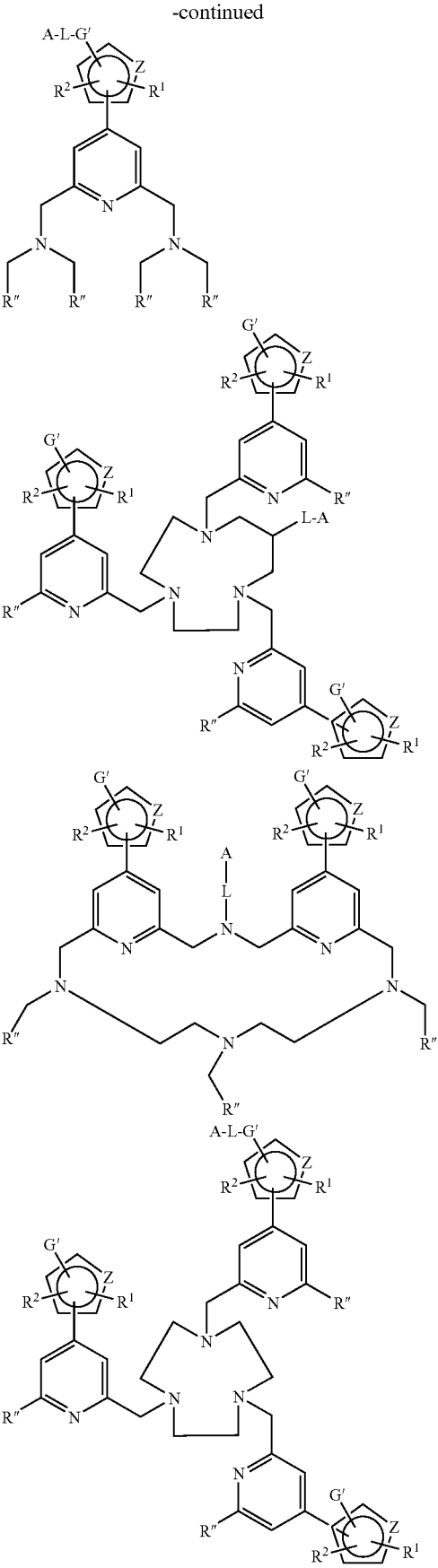

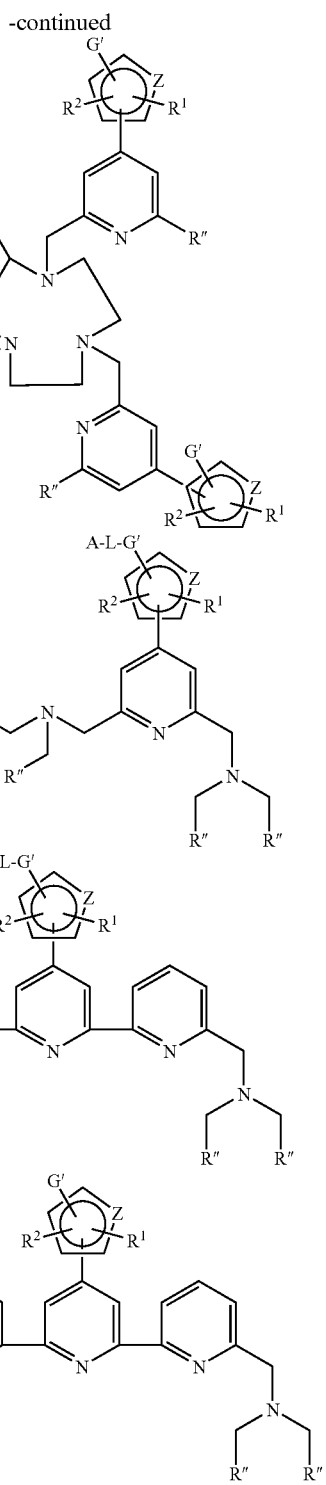

wherein $R^1$ and $R^2$ are electron donating groups, L and G' are as defined in claim 4, and the protecting group $R^3$ is selected from a group consisting of Fmoc, Boc, or Bsmoc, and R" is an alkyl ester or an allyl ester, R'" is an alkyl group, and Z is O or S.

5. A chelating agent comprising;
a chromophoric moiety,
a chelating part comprising at least two carboxylic acid or phosphonic acid esters or amides of said acids, attached to an aromatic unit of the chromophoric moiety, either directly or via a cyclic or acyclic N-containing hydrocarbon chain, and
a reactive group A, tethered to the chromophoric moiety or to the chelating part either directly or via a linker L, said reactive group A enabling binding to a biomolecule or to a functional group on a solid phase, wherein i) the reactive group A is

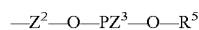

where
one or two of the oxygen atoms is optionally replaced by sulfur,
$Z^3$ is chloro or $NR^6R^7$
$R^5$ is a protecting group,
$R^6$ and $R^7$ are alkyl groups comprising 1-8 carbons,
$Z^2$ is absent or is a radical of a purine base or a pyrimidine base, said base being connected to the oxygen atom via either
   a) a hydrocarbon chain, which is substituted with a protected hydroxymethyl group, or
   b) a furan ring or a pyrane ring, ii) the linker L is formed from one to ten moieties, each moiety being selected from the group consisting of phenylene, alkylene containing 1-12 carbon atoms, ethynydiyl (—C≡C—), ethylenediyl (—C═C—), ether (—O—), thioether (—S—), amide (—CO—NH—, —CO—NR'—, —NH—CO— and —NR'—CO—), carbonyl (—CO—), ester (—COO— and —OOC—), disulfide (—SS—), sulfonamide (—SO$_2$—NH—, —SO$_2$—NR'—), sulfone (—SO$_2$—), phosphate (—O—PO$_2$—O—), diaza (—N═N—), and tertiary amine, wherein R' represents an alkyl group containing less than 5 carbon atoms, iii) the chromophoric moiety comprises one or more aromatic units, wherein at least one of the aromatic units is a furyl or thienyl substituted pyridyl group, wherein the furyl or thienyl group is substituted with one or more, same or different, electron donating groups selected from alkyl and alkoxy groups, and optionally with a carboxylic or sulfonic acid ester or an amide of said acids, G', and wherein the chromophoric moieties are tethered directly to each other to form a terpyridyl group or tethered to each other via a cyclic or acyclic N-containing hydrocarbon chain.

6. A chelating agent according to claim 5 wherein the electron donating groups are selected from the group of methyl, ethyl, n-propyl, i-propyl, n-butyl, t-butyl, sec-butyl, methoxy, ethoxy, n-propoxy, i-propoxy, n-butoxy, t-butoxy and sec-butoxy.

7. A chelating agent according to claim 5 wherein $Z^2$ is a radical of any of the bases thymine, uracil, adenine, guanine or cytosine, and said base is connected to the oxygen atom via
   i) a hydrocarbon chain, which is substituted with a protected hydroxymethyl group, or via
   ii) a furan ring containing a protected hydroxymethyl group in its 4-position and optionally a hydroxyl, protected hydroxyl or modified hydroxyl group in its 2-position.

8. A chelating agent according to claim 6, wherein —$Z^2$—O—P($NR^6R^7$)—O—$R^5$ is selected from the group consisting of;

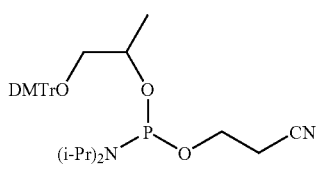
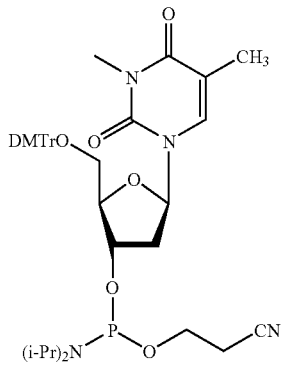
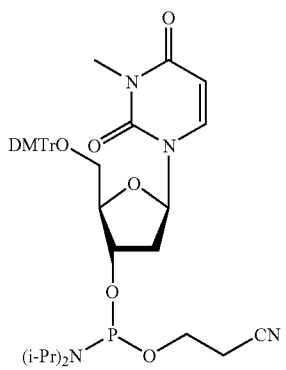
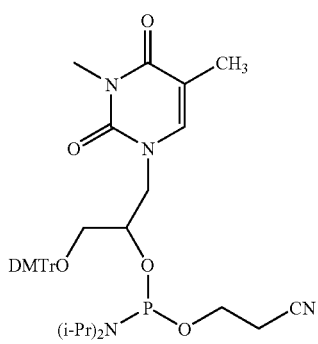
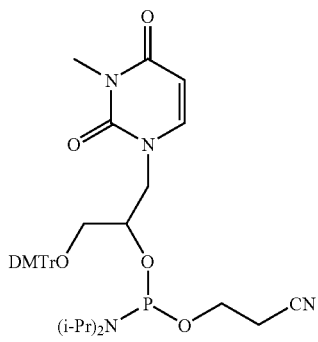
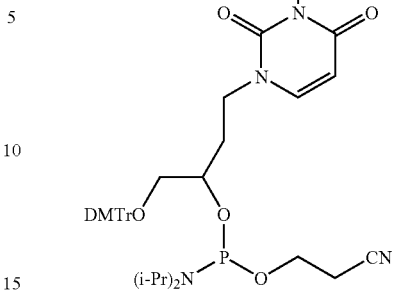
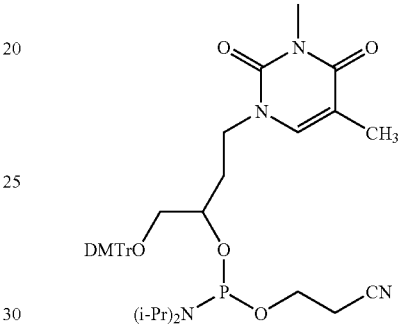
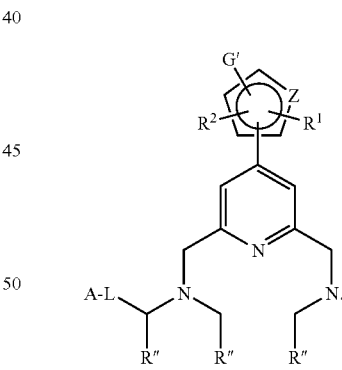
where -L is the position of linker L and DMTr is dimethoxytrityl.
9. A chelating agent according to claim 5, selected from the group consisting of;
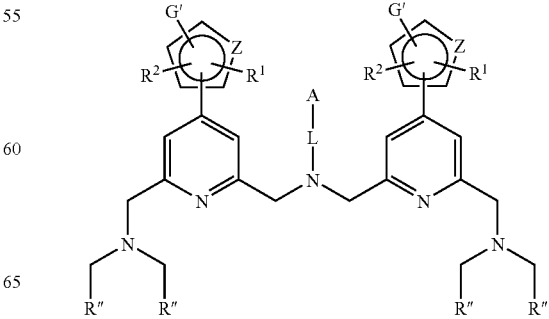

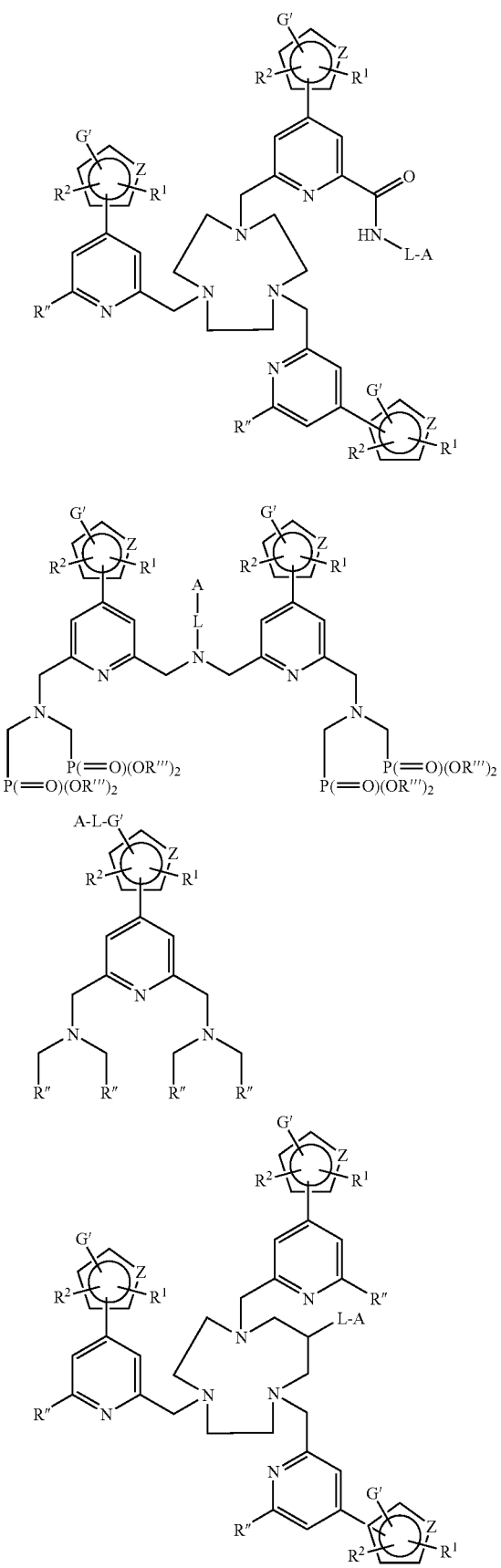
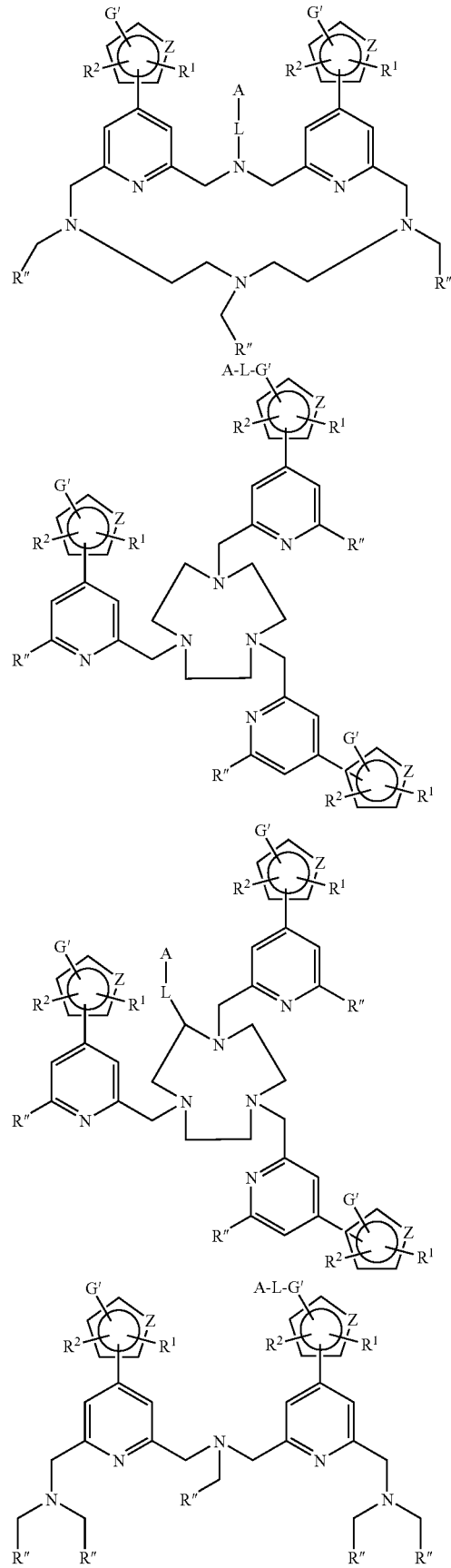

51

-continued

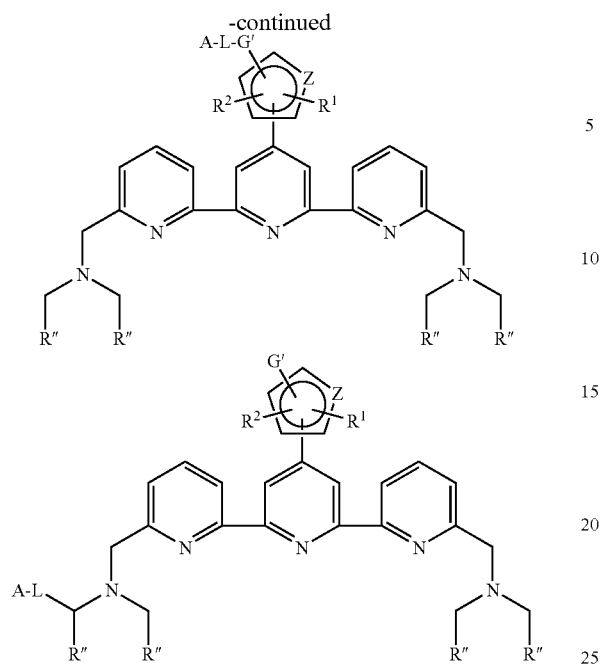

where R″ is an alkyl ester or an allyl ester of a carboxylic acid, R‴ is an alkyl group, and R¹ and R² are electron donating groups, the linker L is formed from one to ten moieties, each moiety being selected from the group consisting of phenylene, alkylene containing 1-12 carbon atoms, ethynydiyl (—C≡C—), ethylenediyl (—C═C—), ether (—O—), thioether (—S—), amide (—CO—NH—, —CO—NR′—, —NH—CO— and —NR′—CO—), carbonyl (—CO—), ester (—COO— and —OOC—), disulfide (—SS—), sulfonamide (—SO₂—NH—, —SO₂—NR′—), sulfone (—SO₂—), phosphate (—O—PO₂—O—), diaza (—N═N—), and tertiary amine, wherein R′ represents an alkyl group containing less than 5 carbon atoms, G′ is a carboxylic acid or sulfonic acid, A is —Z²—O—P(NR⁶R⁷)—O—R⁵ and is selected from the group consisting of:

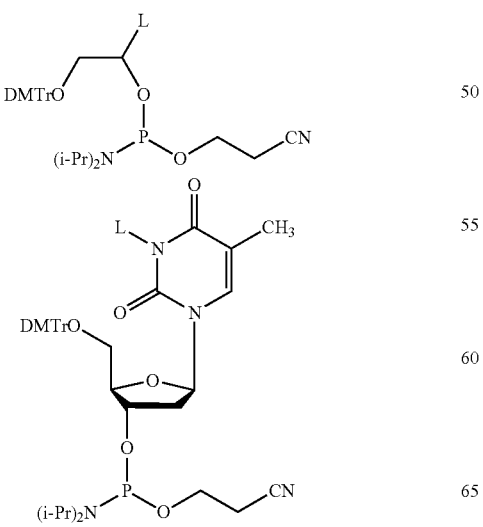

52

-continued

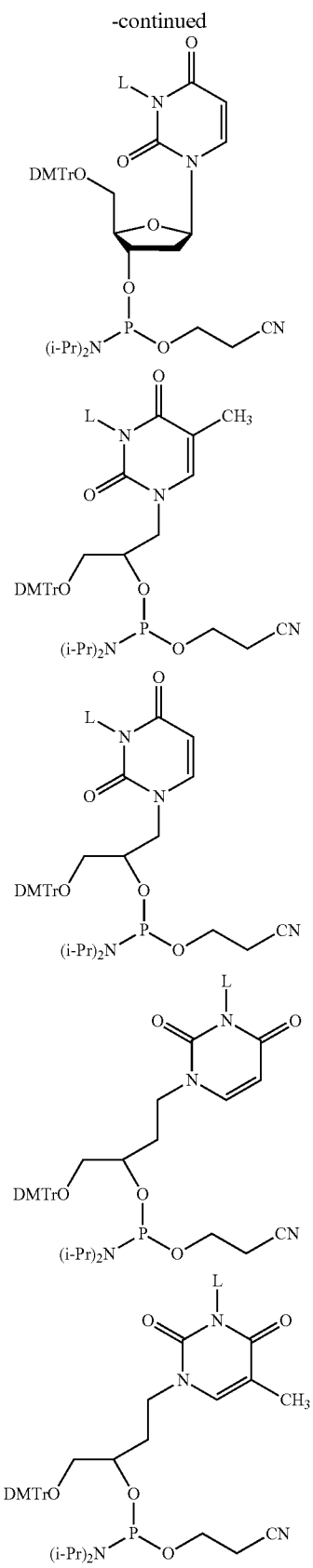

where -L is the position of linker L and DMTr is dimethoxytrityl, and Z is O or S.

10. A biomolecule conjugated with a chelate according to claim 1 biomolecule, wherein the biomolecule is selected from the group consisting of an oligopeptide, oligonucleotide, DNA, RNA, modified oligo- or polynucleotide, protein, oligosaccharide, polysaccharide, phospholipide, PNA, LNA, antibody, steroid, hapten, drug, receptor binding ligand and lectine.

11. A labeled biomolecule, obtained by synthesis on a solid phase, by introduction of a chelating agent according to claim 3 into the oligopeptide structure on an oligopeptide synthesizer, followed by deprotection and optionally also introduction of a metal ion.

12. A labeled oligonucleotide, obtained by synthesis on a solid phase, by introduction of a chelating agent according to claim 5 into the oligonucleotide structure on an oligonucleotide synthesizer, followed by deprotection and optionally also introduction of a metal ion.

13. A solid support conjugated with DNA, RNA, oligopeptide, oligonucleotide, polypeptide, polynucleotide or protein labeled with a chelate according to claim 1.

* * * * *